US009236041B2

(12) United States Patent
Asada et al.

(10) Patent No.: US 9,236,041 B2
(45) Date of Patent: Jan. 12, 2016

(54) FILTER CIRCUIT FOR NOISE CANCELLATION, NOISE REDUCTION SIGNAL PRODUCTION METHOD AND NOISE CANCELING SYSTEM

(75) Inventors: Kohei Asada, Kanagawa (JP); Tetsunori Itabashi, Kanagawa (JP)

(73) Assignee: Sony Corporation, Tokyo (JP)

( * ) Notice: Subject to any disclaimer, the term of this patent is extended or adjusted under 35 U.S.C. 154(b) by 1332 days.

(21) Appl. No.: 11/865,419

(22) Filed: Oct. 1, 2007

(65) Prior Publication Data

US 2008/0112570 A1 May 15, 2008

(30) Foreign Application Priority Data

Nov. 13, 2006 (JP) ................................. 2006-306430

(51) Int. Cl.
*A61F 11/06* (2006.01)
*G10K 11/16* (2006.01)
*G10K 11/178* (2006.01)

(52) U.S. Cl.
CPC .... *G10K 11/1782* (2013.01); *G10K 2210/1053* (2013.01); *G10K 2210/1081* (2013.01)

(58) Field of Classification Search
CPC .................. G10K 11/1782; G10K 2210/1053; G10K 2210/1081
USPC .......... 381/71.1, 71.6, 71.8, 71.11, 71.12, 72, 381/74, 71.13
See application file for complete search history.

(56) References Cited

U.S. PATENT DOCUMENTS 4,833,719 A * 5/1989 Carme et al. .................... 381/72
5,276,740 A 1/1994 Inanaga et al.
6,278,786 B1 * 8/2001 McIntosh .................... 381/71.6
(Continued)

FOREIGN PATENT DOCUMENTS

JP 2-34422 2/1990
JP 02-034422 2/1990
(Continued)

OTHER PUBLICATIONS

"Digital-to-analog converter." Wikipedia. Dec. 16, 2011. pp. 1-6. </en.wikipedia.org/wiki/Digital-to-analog_converter>.*
(Continued)

*Primary Examiner* — Duc Nguyen
*Assistant Examiner* — Kile Blair
(74) *Attorney, Agent, or Firm* — Oblon, McClelland, Maier & Neustadt, L.L.P.

(57) ABSTRACT

There is provided a filter circuit for producing a noise reduction signal for reducing a noise signal collected by a microphone, including: a digital section including an analog/digital conversion section configured to convert the noise signal into a digital noise signal, a digital filter section configured to produce a digital noise reduction signal based on the digital noise signal, and a digital/analog conversion section configured to convert the digital noise reduction signal into an analog noise reduction signal; an analog path connected in parallel to said digital section and configured to output the noise signal as it is or after processed by an analog filter; and a synthesis section configured to synthesize the analog noise reduction signal outputted from said digital/analog conversion section of said digital section and the analog signal outputted from said analog path to produce a noise reduction signal to be used for noise reduction.

22 Claims, 25 Drawing Sheets

(56) References Cited

U.S. PATENT DOCUMENTS

| | | | | |
|---|---|---|---|---|
| 6,449,369 | B1 * | 9/2002 | Carme et al. | 381/71.12 |
| 2001/0046304 | A1 * | 11/2001 | Rast | 381/74 |
| 2003/0228019 | A1 * | 12/2003 | Eichler et al. | 381/71.8 |
| 2007/0253569 | A1 * | 11/2007 | Bose | 381/71.6 |

FOREIGN PATENT DOCUMENTS

| | | | |
|---|---|---|---|
| JP | 3-96199 | | 4/1991 |
| JP | 3-214892 | | 9/1991 |
| JP | 05-313674 | | 11/1993 |
| JP | 5-313674 | | 11/1993 |
| JP | 5-333873 | | 12/1993 |
| JP | 05-333873 | | 12/1993 |
| JP | 08-084728 | A | 4/1996 |
| JP | 08-307986 | | 11/1996 |
| JP | 8-307986 | | 11/1996 |
| JP | 2555702 | B2 | 11/1996 |
| JP | 08-328587 | | 12/1996 |
| JP | 8-328587 | A | 12/1996 |
| JP | 09-097086 | A | 4/1997 |
| JP | 2000-059876 | A | 2/2000 |
| JP | 2003-218651 | | 7/2003 |
| JP | 2006-014307 | | 1/2006 |
| JP | 2006-14307 | | 1/2006 |
| JP | 2006-033174 | | 2/2006 |
| JP | 2006-33174 | | 2/2006 |

OTHER PUBLICATIONS

U.S. Appl. No. 12/015,824, filed Jan. 17, 2008, Asada, et al.

U.S. Appl. No. 11/936,894, filed Nov. 8, 2007, Asada, et al.

U.S. Appl. No. 11/865,354, filed Oct. 1, 2007, Asada.

U.S. Appl. No. 11/868,815, filed Oct. 8, 2007, Itabashi, et al.

U.S. Appl. No. 11/875,374, filed Oct. 19, 2007, Asada.

U.S. Appl. No. 11/936,882, filed Nov. 8, 2007, Asada, et al.

U.S. Appl. No. 11/936,876, filed Nov. 8, 2007, Asada, et al.

U.S. Appl. No. 11/952,468, filed Dec. 7, 2007, Asada, et al.

U.S. Appl. No. 11/966,168, filed Dec. 28, 2007, Ohkuri, et al.

U.S. Appl. No. 11/966,452, filed Dec. 28, 2007, Itabashi, et al.

Office Action issued Aug. 30, 2011 in Japan Application No. 2006-306430.

Office Action issued Jun. 5, 2012 in Japanese Patent Application No. 2006-306430.

Office Action issued Apr. 2, 2013, in Japanese Patent Application No. 2006-306430.

Office Action dated Sep. 24, 2013, in Japanese Patent Application No. 2006-306430.

Office Action issued Nov. 25, 2013 in Korean Patent Application No. 10-2007-0114720 (with English language translation).

Office Action issued May 7, 2014 in Japanese Patent Application No. 2013-137848.

* cited by examiner $$P = \frac{1}{1 + ADHM\beta} N + \frac{AHD}{1 + ADHM\beta} ES \quad \cdots (1)$$

$$\left| \frac{1}{1 + ADHM\beta} \right| < 1 \quad \cdots (2)$$

$$E = (1 + ADHM\beta) \quad \cdots (3)$$

$$P = \frac{1}{1 + ADHM\beta} N + ADHS \quad \cdots (4)$$

FIG. 5
$$P = -F'ADHM\alpha N + FN + ADHS \quad \cdots (1)$$
$$F = F'ADHM\alpha \quad \cdots (2)$$
$$P = ADHS \quad \cdots (3)$$
FIG. 6A
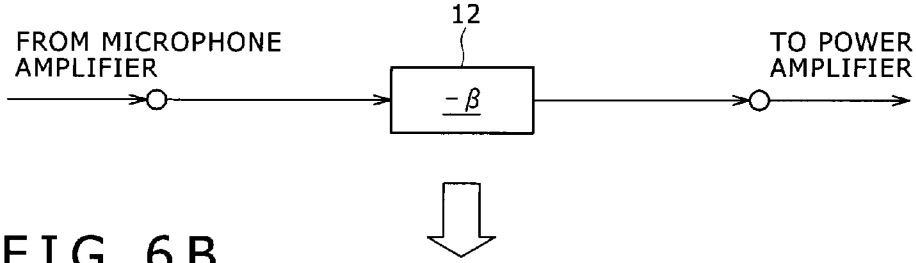
FIG. 6B
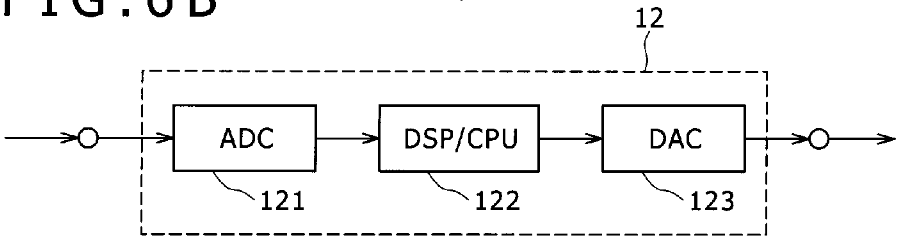
FIG. 6C
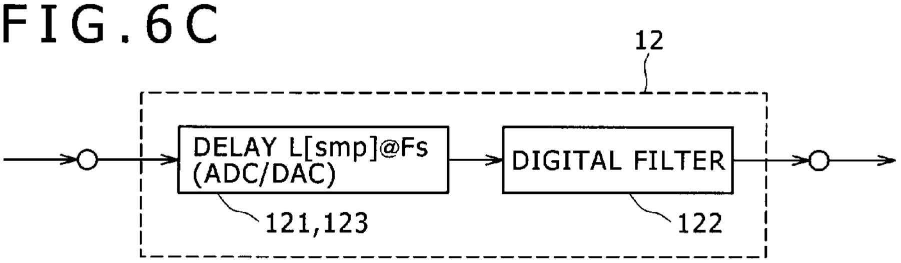

FIG.12
$$Hb(z) = z^{-L} Hx(z) + Ha(z) \quad \cdots (1)$$
$$Hx(z) = z^{+L} (Hb(z) - Ha(z)) \quad \cdots (2)$$
FIG.13A
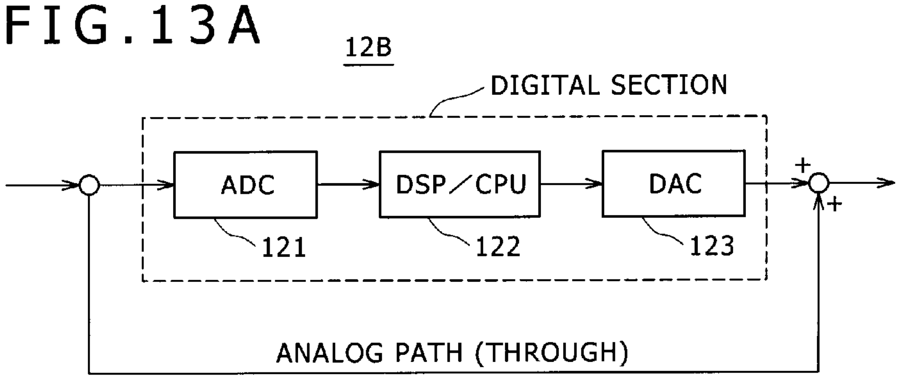
FIG.13B
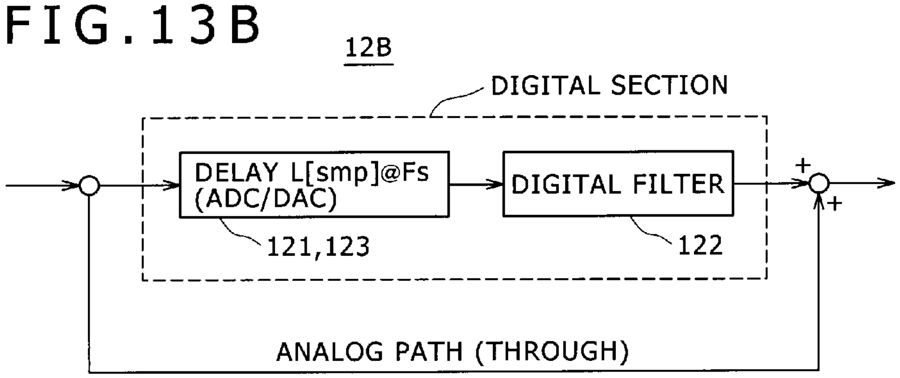

12E

FILTER CIRCUIT FOR NOISE CANCELLATION, NOISE REDUCTION SIGNAL PRODUCTION METHOD AND NOISE CANCELING SYSTEM

CROSS REFERENCES TO RELATED APPLICATIONS

The present invention contains subject matter related to Japanese Patent Application JP 2006-306430 filed in the Japan Patent Office on Nov. 13, 2006, the entire contents of which being incorporated herein by reference.

BACKGROUND OF THE INVENTION

1. Field of the Invention

This invention relates to a filter circuit and a noise reduction signal production method for a noise canceling system which are applied, for example, to a headphone for allowing a user to enjoy reproduced music or the like, a headset for reducing noise and a like apparatus and a noise canceling system which uses such a filter circuit and a noise reduction signal production method as just mentioned.

2. Description of the Related Art

An active noise reduction system incorporated in a headphone is available in the related art. The noise reduction system is called also noise canceling system. Therefore, such a noise reduction system as mentioned above is hereinafter referred to as noise canceling system. Noise canceling systems which are placed in practical use at present are all implemented in the form of an analog circuit and are classified into two types including the feedback type and the feedforward type.

A noise reduction apparatus is disclosed, for example, in Japanese Patent Laid-Open No. Hei 3-214892 (hereinafter referred to as Patent Document 1). In the noise reduction apparatus of Patent Document 1, a microphone unit is provided in an acoustic tube to be attached to an ear of a user. Internal noise of the acoustic tube collected by the microphone unit is inverted in phase and emitted from an earphone set provided in the proximity of the microphone unit thereby to reduce external noise.

A noise reduction headphone is disclosed in Japanese Patent Laid-Open No. Hei 3-96199 (hereinafter referred to as Patent Document 2). In the noise reduction headphone of Patent Document 2, when it is attached to the head of a user, a second microphone is positioned between the headphone and the auditory meatus. An output of the second microphone is used to make the transmission characteristic from a first microphone, which is provided in the proximity of the ear when the headphone is attached to the head of the user and collects external sound, to the headphone same as the transmission characteristic of a path along which the external noise reaches the meatus. The noise reduction headphone thereby reduces external noise irrespective of in what manner the headphone is attached to the head of the user.

SUMMARY OF THE INVENTION

Where it is intended to form noise canceling systems of the feedback type and the feedforward type, which are composed of analog circuits in the related art, from digital circuits, if it is tried to use a sigma-delta ($\Sigma\cdot\Delta$) type analog/digital converter (hereinafter referred to simply as ADC) or a digital/analog converter (hereinafter referred to simply as DAC), then they give rise to a problem that they exhibit significant digital delay and fails in achievement of sufficient noise reduction. Although an ADC or a DAC of the sequential conversion type which can perform high speed conversion is available even in a current situation, they are actually designed for military or business applications and are expensive. Therefore, it is difficult to adopt them in a noise reduction system to be incorporated in consumer appliances.

However, "digitalization formation" of a noise canceling system or active noise reduction system for a headphone or a like apparatus has a merit that it enhances the performance in use as viewed from the user in that a system which allows automatic selection among a plurality of modes or manual selection among such modes by the user can be configured. In addition, also as regards the reproduction quality, a high sound quality performance can be anticipated by adopting digital equalization by which fine control can be achieved.

Therefore, it is demanded to provide a filter circuit, a noise reduction signal production method and a noise canceling system by which the influence of digital delay, which is a principal cause of failure in achievement of sufficient noise reduction by existing digital processing, is suppressed to achieve reduction of noise appropriately while such merits by digitalized formation as described are maintained.

According to an embodiment of the present invention, there is provided a filter circuit for producing a noise reduction signal for reducing a noise signal collected by a microphone, including a digital section including an analog/digital conversion section configured to convert the noise signal into a digital noise signal, a digital filter section configured to produce a digital noise reduction signal based on the digital noise signal, and a digital/analog conversion section configured to convert the digital noise reduction signal into an analog noise reduction signal, an analog path connected in parallel to the digital section and configured to output the noise signal as it is or after processed by an analog filter, and a synthesis section configured to synthesize the analog noise reduction signal outputted from the digital/analog conversion section of the digital section and the analog signal outputted from the analog path to produce a noise reduction signal to be used for noise reduction.

The filter circuit is used with a noise canceling system. In the circuit, the analog path configured to output the noise signal as it is or after processed by an analog filter is connected in parallel to the digital section which includes the analog/digital conversion section, digital filter section and digital/analog conversion section. The analog noise reduction signal produced by the digital section and the analog signal outputted from the analog path are synthesized by the synthesis section to produce a noise reduction signal to be used for noise reduction.

Consequently, the noise reduction signal formed by the digital section and the analog signal from the analog path, that is, the noise reduction signal formed by the analog path, compensate for each other in terms of the frequency band in which noise reduction is possible and the noise reduction level. Consequently, the frequency band and the noise reproduction level can be assured sufficiently. Further, merits by digitalized formation by provision of the digital section, that is, setting or selection of a plurality of modes and implementation of a digital equalization function and so forth, can be anticipated, and the use performance as viewed from the user can be enhanced.

According to another embodiment of the present invention, there is provided a noise canceling system of the feedback type, including a microphone disposed inside a housing to be attached to an ear portion of a user and configured to collect a noise signal leaking into the inside of the housing, a filter circuit configured to form a noise reduction signal for reducing noise from the noise signal collected by the microphone, an amplification section configured to amplify the noise reduction signal formed by the filter circuit, and a driver configured to emit sound into the housing based on the noise reduction signal from the amplification section, the filter circuit including a digital section which in turn includes an analog/digital conversion section configured to receive supply of the noise signal collected by the microphone and convert the noise signal into a digital signal, a digital filter section configured to receive supply of the digital noise signal from the analog/digital conversion section and form a noise reduction signal from the digital noise signal, and a digital/analog conversion section configured to receive supply of the noise reduction signal from the digital filter section and convert the noise reduction signal into an analog signal, the filter circuit further including an analog path connected in parallel to the digital section and configured to output the noise signal collected by the microphone as it is or after processed by an analog filter, and a synthesis section configured to synthesize the noise reduction signal in the form of an analog signal outputted from the digital/analog conversion section of the digital section and the analog signal from the analog path to produce a noise reduction signal to be used for noise reduction.

In the noise canceling system, a noise reproduction signal is produced from a noise signal collected by the microphone provided inside the housing to be attached to the ear portion of a user. The noise canceling system includes the digital section and the analog path connected in parallel to the filter circuit which produces the noise reduction signal.

Consequently, the noise reduction signal formed by the digital section and the analog signal from the analog path, that is, the noise reduction signal formed by the analog path, compensate for each other in terms of the frequency band in which noise reduction is possible and the noise reduction level. Consequently, the frequency band and the noise reproduction level can be assured sufficiently. Also merits by digitalized formation by provision of the digital section can be enjoyed.

The noise canceling system may further include a sound quality adjustment section configured to receive supply of a sound signal of an object of reproduction and perform sound quality adjustment based on the sound signal, a reproduction sound amplification section configured to receive supply of the sound signal having the adjusted sound quality from the sound quality adjustment section and amplify the received sound signal, and a reproduction driver configured to receive supply of the sound signal amplified by the reproduction sound amplification section and emit sound into the inside of the housing in response to the sound signal.

In the noise canceling system, the noise canceling system of the feedback type which includes the filter circuit which in turn includes the digital section and the analog path connected in parallel and the system which includes the sound quality adjustment section, reproduction sound amplification section and reproduction driver which process input sound from the outside can function simultaneously.

With the noise canceling system, while noise is reduced effectively, a sound signal from the outside can be reproduced so as to be enjoyed by the user. In this instance, merits provided by digitalized formation of the filter circuit as well as merits of enhancement of the sound quality by the function of the sound quality adjustment section can be enjoyed.

Or, the noise canceling system may further include a noise canceling system section of the feedforward type which in turn includes a second microphone provided outside the housing to be attached to the ear portion of the user and configured to collect a noise signal from a noise source, a second filter circuit configured to form a second noise reduction signal for reducing noise from the noise signal collected by the second microphone, a second amplification section configured to amplify the second noise reduction signal formed by the second filter circuit, and a second driver configured to emit sound into the housing based on the second noise reduction signal from the second amplification section.

The noise canceling system is implemented as a noise canceling system which can simultaneously use both of a noise canceling system of the feedback type wherein the digital second and the analog path are connected in parallel and a noise canceling system of the feedforward type. Consequently, reduction of noise can be achieved with a higher degree of quality. Further, with the noise canceling system of the feedback type, also merits provided by digitalized formation of the filter circuit can be enjoyed.

In this instance, the noise canceling system may further include an input sound reproduction processing section including a sound quality adjustment section configured to receive supply of a sound signal of an object of reproduction and perform sound quality adjustment based on the sound signal, a reproduction sound amplification section configured to receive supply of the sound signal having the adjusted sound quality from the sound quality adjustment section and amplify the received sound signal, and a reproduction driver configured to receive supply of the sound signal amplified by the reproduction sound amplification section and emit sound into the inside of the housing in response to the sound signal, and a changeover section configured to selectively render the noise canceling system section of the feedforward type and the input sound reproduction processing section operative.

In the noise canceling system, it can be selectively set whether or not the noise canceling system of the feedforward type should be rendered operative or the input sound reproduction processing section for processing input sound should be rendered operative together with the noise canceling system of the feedback type which has the filter circuit which includes the digital section and the analog path connected in parallel.

With the noise canceling system, if the noise canceling system of the feedforward type is selectively rendered operative, then noise reduction of a high degree of quality can be performed thereby to form a no-sound state of a high degree of quality. On the other hand, if the input sound reproduction processing section is selectively rendered operative, then sound of an inputted reproduction object can be reproduced so as to be enjoyed by the user while noise is suppressed by the noise canceling system of the feedback type. Further, whichever one of the noise canceling system of the feedforward type and the input sound reproduction processing section is rendered operative, merits provided by digitalized formation of the filter circuit of the noise canceling system of the feedback type can be enjoyed.

In summary, with the filter circuit and the noise canceling system, the noise reduction signal formed by the digital section and the analog signal from the analog path, that is, the noise reduction signal formed by the analog path, compensate for each other in terms of the frequency band in which noise reduction is possible and the noise reduction level. Consequently, the frequency band and the noise reproduction level can be assured sufficiently.

Further, merits by digitalized formation by provision of the digital section, that is, setting or selection of a plurality of modes and implementation of a digital equalization function and so forth, can be anticipated, and the use performance as viewed from the user can be enhanced.

The above and other features and advantages of the present invention will become apparent from the following description and the appended claims, taken in conjunction with the accompanying drawings in which like parts or elements denoted by like reference symbols.

BRIEF DESCRIPTION OF THE DRAWINGS

FIG. 5 is a view illustrating calculation expressions representative of characteristics of the noise canceling system of the feedforward type shown in FIG. 2;

FIGS. 6A, 6B and 6C are block diagrams showing an example of a configuration where an FB filter circuit of the noise canceling system of the feedback type shown in FIG. 1B is formed as a digital circuit;

FIG. 12 is a view illustrating a characteristic of the FB filter circuit of FIG. 11B and a characteristic of a digital filter section shown in FIG. 11B;

FIGS. 13A and 13B are block diagrams showing another example of the configuration of the FB filter circuit according to the present invention;

DETAILED DESCRIPTION OF THE PREFERRED EMBODIMENT

Noise Canceling System

A system which actively reduces external noise, that is, a noise canceling system, begins to be popularized in headphones and earphones. Almost all noise canceling systems placed on the market are formed from analog circuits and roughly classified into the feedback type and the feedforward type in terms of the noise canceling technique.

Before a preferred embodiment of the present invention is described, examples of a configuration and operation principle of a noise canceling system of the feedback type and examples of a configuration and operation principle of a noise canceling system of the feedforward type are described with reference to FIGS. 1A to 5.

[Noise Canceling System of the Feedback Type]

First, a noise canceling system of the feedback type is described. FIG. 1A shows a configuration for the right channel side where a headphone system to which a noise canceling system of the feedback type is applied is attached to the head of a user, that is, to the user head HD. Meanwhile, FIG. 1B shows a general configuration of the noise canceling system of the feedback type.

Where the feedback system is applied, generally a microphone 111 is positioned inside a headphone housing (housing section) HP as seen in FIG. 1A. An antiphase component (noise reduction signal) to a signal (noise signal) collected by the microphone 111 is fed back and used for servo control to reduce the noise which is to enter the headphone housing HP from the outside. In this instance, the position of the microphone 111 becomes a cancel point or control point CP which corresponds to the position of the ear of the user. Therefore, the microphone 111 is frequently placed at a position proximate to the ear of the user, that is, on a front face of a diaphragm of an equalizer 16 taking a noise reduction effect into consideration.

Figure 1B:
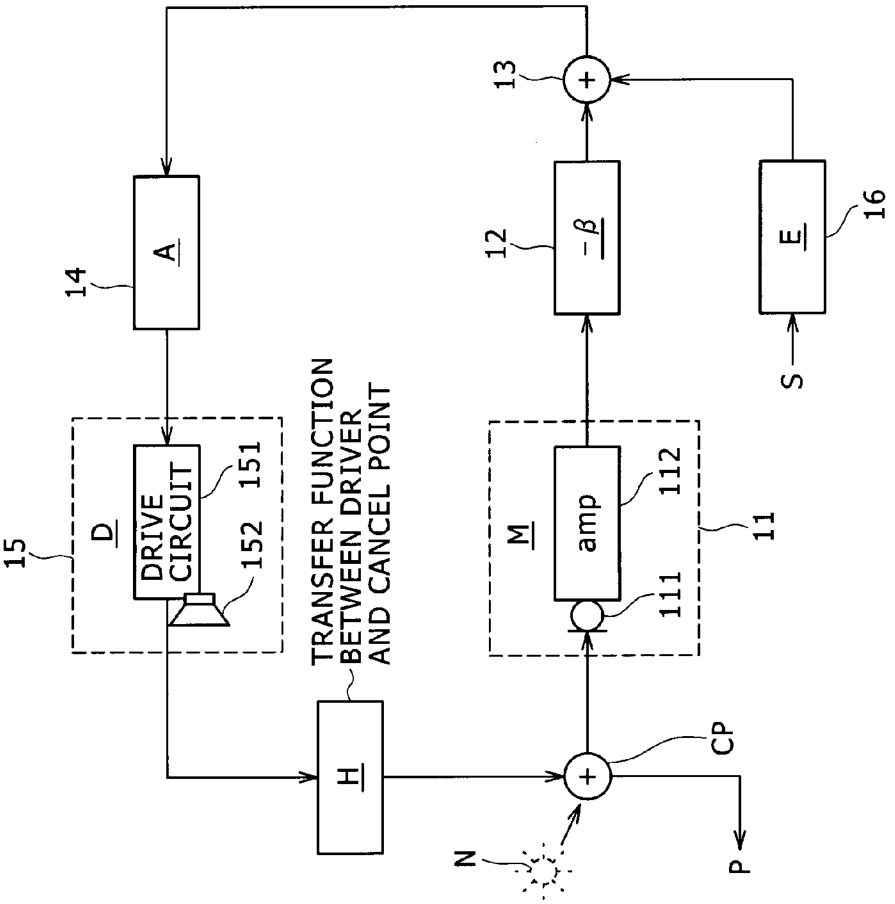
FIGS. 1A and 1B are a schematic view and a block diagram, respectively, showing a noise canceling system of the feedback type.
Figure 1A:
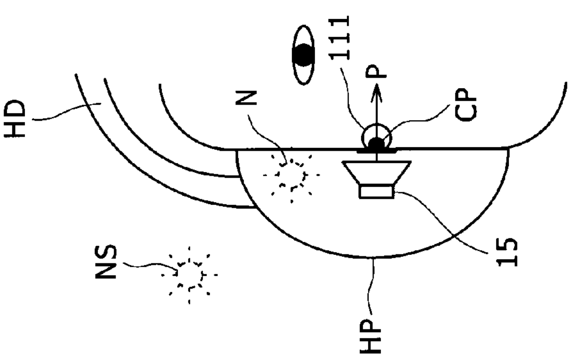

The noise canceling system of the feedback type is described more particularly with reference to FIG. 1B. The noise canceling system of the feedback type shown in FIG. 1B includes a microphone and microphone amplification section 11 including a microphone 111 and a microphone amplifier 112. The noise canceling system further includes a filter circuit (hereinafter referred to as FB filter circuit) 12 designed for feedback control, a synthesis section 13, a power amplifier 14, a driver 15 including a drive circuit 151 and a speaker 152, and an equalizer 16.

The characters A, D, M and $-\beta$ described in blocks shown in FIG. 1B represent transfer functions of the power amplifier 14, driver 15, microphone and microphone amplification section 11 and FB filter circuit 12, respectively. Similarly, the character E in the block of the equalizer 16 represents the transfer function of the equalizer 16 to be multiplied to a signal S of an object of hearing, and the character H of a block placed between the driver 15 and the cancel point CP represents the transfer function of the space from the driver 15 to the microphone 111, that is, the transfer function between the driver and the cancel point. The transfer functions mentioned are represented in complex representations.

Referring to FIGS. 1A and 1B, the character N represents noise entering from a noise source NS on the outside to a portion around the position of the microphone in the headphone housing HP, and the character P represents the sound pressure or output sound coming to the ear of the user. The cause of the entrance of the noise N into the headphone housing HP is, for example, sound leaking as a sound pressure from a gap of the ear pad of the headphone housing HP or sound transmitted to the inside of the housing as a result of vibration of the headphone housing HP caused by such sound pressure applied thereto.

Figures 3, 4:
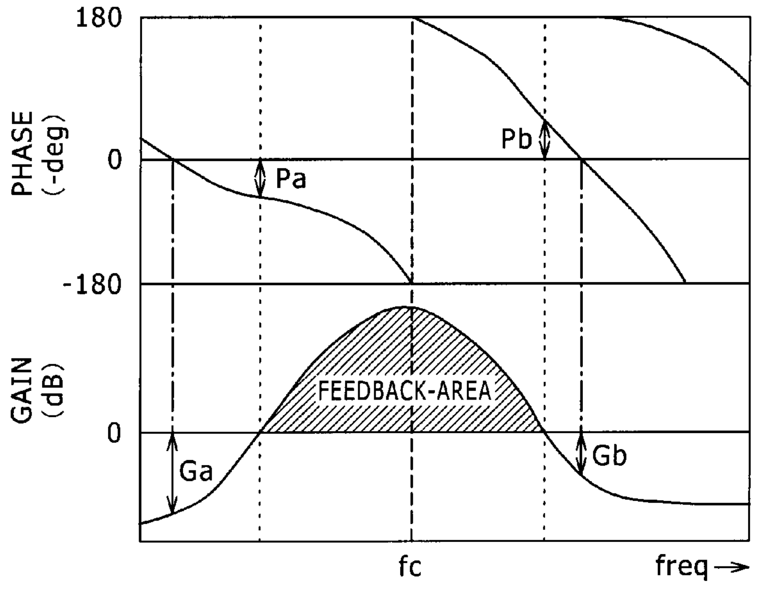
FIG. 3 is a view illustrating calculation expressions representative of characteristics of the noise canceling system of the feedback type shown in FIG. 1.
FIG. 4 is a board diagram illustrating a phase margin and a gain margin in the noise canceling system of the feedback type.

At this time, the sound pressure P coming to the ear of the user in FIG. 1B can be represented by an expression (1) in FIG. 3. If attention is paid to the noise N in the expression (1) in FIG. 3, it can be recognized that the noise N attenuates to $1/(1+ADHM\beta)$. In order for the system of the expression (1) of FIG. 3 to operate stably as a noise canceling mechanism within a noise reduction object frequency band, it is necessary for an expression (2) in FIG. 3 to be satisfied.

Generally, since the absolute value of the product of the transfer functions in a noise canceling system of the feedback type is higher than 1 ($1<<ADHM\beta$), the stability of the system according to the expression (2) of FIG. 3 can be interpreted in the following manner together with decision of the stability of Nyquist in old control theories.

An "open loop" produced when a loop relating to the noise N is cut at one place ($-ADHM\beta$) in FIG. 1B is considered. For example, if the cut portion is provided between the microphone and microphone amplification section 11 and the FB filter circuit 12, then an "open loop" can be formed. This open loop has such a characteristic as is represented, for example, by such a board diagram as seen in FIG. 4.

Where this open loop is selected as an object, from the stability decision of Nyquist, two conditions of (1) that, when the phase passes a point of 0 degree, the gain must be lower than 0 dB (0 decibel) and (2) that, when the gain is higher than 0 dB, the phase must not include a point of 0 degree.

If any of the conditions (1) and (2) above is not satisfied, then positive feedback is applied to the loop, resulting in oscillation (howling) of the loop. In FIG. 4, reference characters Pa and Pb individually represent a phase margin, and Ga and Gb individually represent a gain margin. Where such margins are small, the possibility of oscillation is high depending upon the personal differences among users who utilize a headphone to which the noise canceling system is applied and upon the dispersion in mounting of the headphone.

In particular, the axis of abscissa in FIG. 4 indicates the frequency while the axis of ordinate indicates the gain and the phase at lower and upper halves thereof, respectively. Then, when the phase passes a point of 0 degree, as seen from the gain margins Ga and Gb in FIG. 4, if the gain is lower than 0 dB, then positive feedback is applied to the loop, resulting in oscillation. However, when the gain is equal to or higher than 0 dB, unless the phase does not include a point of 0 degree, positive feedback is applied to the loop, resulting in oscillation, as seen from the phase margins Pa and Pb in FIG. 4.

Now, reproduction of necessary sound from the headphone in which the noise securing system of the feedback type shown in FIG. 1B is incorporated is described in addition to the noise reduction function described above. The input sound S in FIG. 1B is a general term of a sound signal to be reproduced originally by the driver of the headphone such as, for example, a music signal from a music reproduction apparatus, sound of the microphone outside the housing (where the headphone is used as a hearing aid function) or a sound signal by communication such as telephone communication (where the headphone is used as a headset).

If attention is paid to the input sound S in the expression (1) in FIG. 3, the transfer function E of the equalizer 16 can be represented by the expression (3) in FIG. 3. Further, if also the transfer function E of the equalizer 16 in the expression (3) of FIG. 3 is taken into consideration, the sound pressure P of the noise canceling system of FIG. 1B can be represented by an expression (4) in FIG. 3.

If it is assumed that the position of the microphone 111 is very proximate to the position of the ear, then since the character H represents the transfer function from the driver 15 to the microphone (ear) 111 and the characters A and D represent the transfer functions of the power amplifier 14 and the driver 15, respectively, it can be recognized that a characteristic similar to that of an ordinary headphone which does not have the noise reduction function is obtained. It is to be noted that the transfer function E of the equalizer 16 in this instance is substantially equivalent to an open loop characteristic as viewed on the frequency axis.

[Noise Canceling System of the Feedforward Type]

Now, a noise canceling system of the feedforward type is described. FIG. 2A shows a configuration for the right channel side where a headphone system to which a noise canceling system of the feed forward type is applied is attached to the head of a user, that is, to a user head HD. Meanwhile, FIG. 2B shows a general configuration of the noise canceling system of the feedforward type.

In the noise canceling system of the feedforward type, a microphone 211 is basically disposed outside a headphone HP as seen in FIG. 2A. Then, noise collected by the microphone 211 is subjected to a suitable filtering process and then reproduced by a driver 25 provided inside the headphone housing HP so that the noise is canceled at a place proximate to the ear.

Figure 2B:
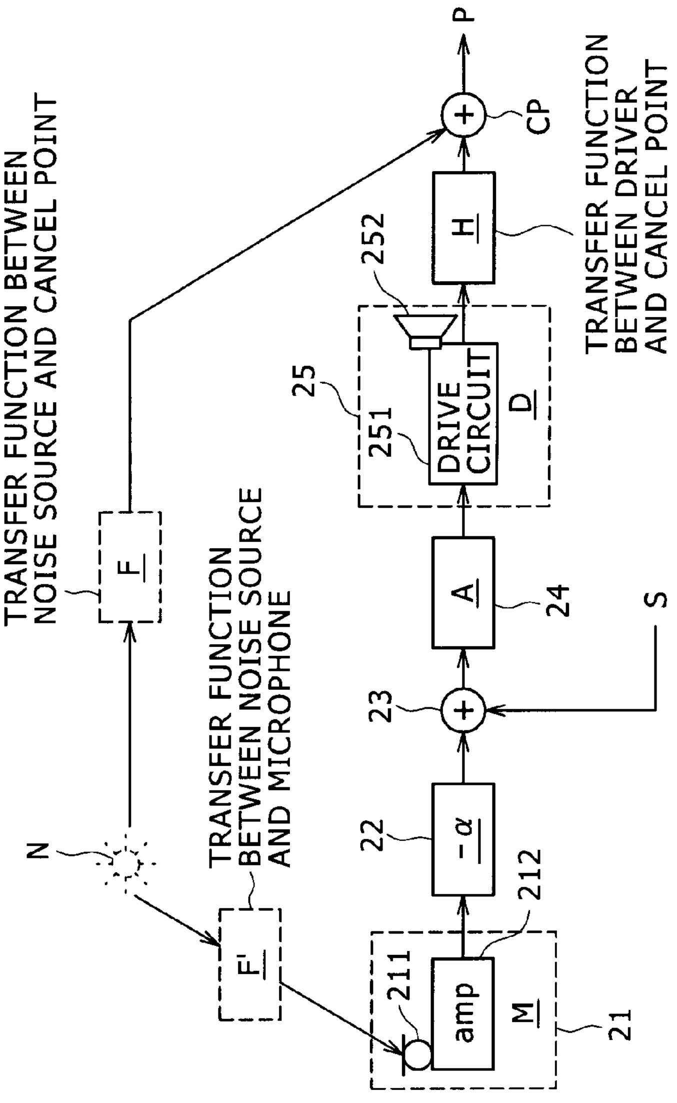
FIGS. 2A and 2B are a schematic view and a block diagram, respectively, showing a noise canceling system of the feedforward type.
Figure 2A:
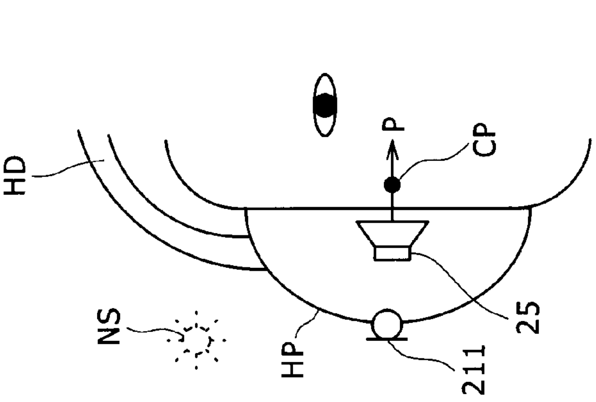

The noise canceling system of the feedforward type is described more particularly with reference to FIG. 2B. The noise canceling system of the feedforward type shown in FIG. 2B includes a microphone and microphone amplification section 21 including a microphone 211 and a microphone amplifier 212. The noise canceling system further includes a filter circuit (hereinafter referred to as FF filter circuit) 22 designed for feedforward control, a synthesis section 23, a power amplifier 24, and a driver 25 including a drive circuit 251 and a speaker 252.

Also in the noise canceling system of the feedforward type shown in FIG. 2B, the characters A, D and M described in blocks represent transfer functions of the power amplifier 24, driver 25 and microphone and microphone amplification section 21, respectively. Further, in FIG. 2, the character N represents an external noise source. The principal reason in entrance of noise into the headphone housing HP from the noise source N is such as described hereinabove in connection with the noise canceling system of the feedback type.

Further, in FIG. 2B, the transfer function from the position of the external noise N to the cancel point CP, that is, the transfer function between the noise source and the cancel point, is represented by the character F. Further, the transfer function from the noise source N to the microphone 211, that is, the transfer function between the noise source and the microphone, is represented by the character F'. Furthermore, the transfer function from the driver 25 to the cancel point (ear position) CP, that is, the transfer function between the driver and the cancel point, is represented by the character H.

Then, if the transfer function of the FF filter circuit 22 which makes the core of the noise canceling system of the feedforward type is represented by $-\alpha$, then the sound pressure or output sound P coming to the ear of the user in FIG. 2B can be represented by an expression (1) in FIG. 5.

Here, if ideal conditions are considered, then the transfer function F between the noise source and the cancel point can be presented by an expression (2) in FIG. 5. Then, if the expression (2) in FIG. 5 is substituted into the expression (1) in FIG. 5, then since the first term and the second term cancel each other, the sound pressure P in the noise canceling system of the feedforward type shown in FIG. 2B can be represented by an expression (3) in FIG. 5. From the expression (3), it can be recognized that the noise is canceled while only the music signal or the object sound signal or the like to be heard remains and sound similar to that in ordinary headphone operation can be enjoyed.

Actually, however, it is difficult to obtain a configuration of a complete filter having such transfer functions that the expression (2) illustrated in FIG. 5 is satisfied fully. Particularly in middle and high frequency regions, usually such an active noise reduction process as described above is not performed but passive sound interception by the headphone housing is applied frequently from such reasons that the individual differences are great in that the shape of the ear differs among different persons and the attaching state of a headphone differs among different persons and that the characteristics vary depending upon the position of noise and the position of the microphone. It is to be noted that the expression (2) in FIG. 5 signifies, as apparent from the expression itself, that the transfer function from the noise source to the ear position can be imitated by an electric circuit including the transfer function $\alpha$.

It is to be noted that, different from that in the noise canceling system of the feedback type, the cancel point CP in the noise canceling system of the feedforward type shown in FIGS. 2A and 2B can be set to an arbitrary ear position of the user as seen in FIG. 2A. However, in an ordinary case, the transfer function $\alpha$ is fixed and is determined aiming at some target characteristic in advance at a design stage. Therefore, there is the possibility that such a phenomenon may occur that, since the shape of the ear differs among different users, a sufficient noise cancel effect is not achieve or a noise component is added but not in an inverted phase, resulting in generation of abnormal sound.

From those, the noise canceling systems of the feedback type and the feedforward type generally have different characteristics in that, while the noise canceling system of the feedforward type is low in possibility of oscillation and hence is high in stability, it is difficult to obtain a sufficient attenuation amount whereas the noise canceling system of the feedforward type requires attention to stability of the system while a great attenuation amount can be expected.

A noise reduction headphone which uses an adaptive signal processing technique is proposed separately. In the case of a noise reduction headphone which uses the adaptive signal processing technique, a microphone is provided on both inside and outside a headphone housing. The inside microphone is used to analyze an error signal for cancellation with a filter processing component and produce and update a new adaptive filter. However, since noise outside of the headphone housing is basically processed by a digital filter and reproduced, the noise reduction headphone generally has a form of a feedforward system.

[Necessity for and Problems of Digitalized Formation of a Noise Canceling System]

While noise canceling systems formed from analog circuits of the feedback type and the feedforward type are implemented as described above, it is demanded to form such noise canceling systems from digital circuits. Also a technique of performing noise cancellation using an adaptive signal process which exhibits no delay even where the FB filter circuit 12 or the FF filter circuit 22 is formed from a digital filter has been proposed.

However, from the problem of the stability of the system and from such problems that an increased process scale is needed, that the object of reduction is directed only to periodic noise waveforms and that a high effect cannot be achieved while a high cost is needed, it is a situation at present that a technique of forming a digital filter using an adaptive signal process to achieve noise cancellation has not been commercialized as yet.

In the following, the necessity for digitalized formation of a noise canceling system and problems involved in digitalized formation in which an adaptive signal process is not used are described particularly. Further, the invention which solves the problems is described particularly.

It is to be noted that, in the following description, for simplified description, principally an application to a noise canceling system of the feedback type which exhibits a high noise attenuation effect is described as an example. However, also with regard to a noise canceling system of the feedforward type, the necessity for and problems in digitalization exist, and the present invention can solve the problems similarly.

[Necessity for Digitalized Formation of a Noise Canceling System]

First, the necessity for digitalized formation of a noise canceling system is described. If the FB filter circuit 12 which is a transfer function $(-\beta)$ section in the noise canceling system of the feedback type can be formed in digitalized formation, then such merits as described in (1) to (4) below can be enjoyed.

In particular, (1) a system which allows automatic selection or manual operation by a user of a plurality of modes and the use performance as viewed from the user is raised. (2) As a digital filter which allows fine control is used, control quality of a high degree of accuracy which exhibits a reduced dispersion can be achieved, resulting in increase of the noise reduction amount and the reduction frequency band.

Further, (3) since the filter shape can be changed by modification to software for an arithmetic operation processing device (digital signal processor (DSP)/central processing unit (CPU)) without changing the number of parts, alteration involved in change of the system design or device characteristics is facilitated. (4) Since the same ADC/DAC and DSP/CPU are used also for an external input such as music reproduction or telephone conversation, high sound quality reproduction can be anticipated by applying digital equalization of a high degree of accuracy also for such external input signals.

If the FB filter circuit 12 can be formed in digitalized formation in this manner, then flexible control becomes possible for various cases, and a system can be configured which can cancel noise in high quality irrespective of a user who uses the system.

[Problems in Digitalized Formation of a Noise Canceling System]

However, as described hereinabove, only a system whose portion corresponding to the FB filter circuit 12 is formed from an analog circuit is placed in practical use as a noise canceling system of the feedback type. It is possible to configure the FB filter circuit 12, which is formed from an analog circuit, otherwise from a digital circuit by using an ADC, a DSP or a CPU which forms a digital filter processing mechanism (arithmetic operation processing section), a DAC and so forth.

However, the FB filter circuit 12 having a configuration of a digital circuit needs much time for processing. Therefore, the FB filter circuit 12 gives rise to delay of a signal of a processing object and fails to appropriately cancel noise. This makes a factor of obstruction to the digitalized formation. If the factor of obstruction to the digitalized formation is studied more particularly, then it is considered that the delay of a signal described above is caused principally by the delay by the ADC and the DAC inserted forwardly and backwardly of the arithmetic operation processing section (arithmetic operation processing apparatus) formed from a DSP and a CPU (hereinafter referred to as DSP/CPU) rather than by the digital filter processing mechanism (arithmetic operation processing section for producing a noise reduction signal for reducing noise) formed from a DSP/CPU.

FIGS. 6A, 6B and 6C show an example of a configuration of the FB filter circuit 12 of the noise canceling system of the feedback type described hereinabove with reference to FIG. 1B where the FB filter circuit 12 is formed in digitalized formation. While the FB filter circuit 12 is shown in a single block also in FIG. 1B, in order to form the FB filter circuit 12 which is shown in a single block in FIG. 6A in digitalized formation, the FB filter circuit 12 is formed from an ADC 121, a DSP/CPU 122 and a DAC 123 as seen in FIG. 6B. Although a digital filter can be configured comparatively freely as software in the DSP/CPU 122, it is influenced much by delay by filters built in the ADC 121 and the DAC 123.

Here, the ADC 121 is a block for converting a signal (noise signal) collected by the microphone 111 and amplified by the microphone amplifier 112 into a digital signal, that is, a digital noise signal. Meanwhile, the DSP/CPU 122 is a block which forms a noise reduction signal having a phase opposite to that of the noise signal and capable of canceling the noise signal taking the transfer functions of the associated circuit sections and the transfer functions between the driver and the cancel point and so forth into consideration. Further, the DAC 123 is a block which converts a noise reduction signal in the form of a digital signal formed by the DSP/CPU 122 into an analog signal.

If the configuration of the FB filter circuit 12 shown in FIG. 6B is represented functionally, then it can be represented as being formed from a digital filter section 121, 123 for generating delay L and a digital filter section 122 formed from the DSP/CPU. Then, in the digitalized FB filter circuit 12, a delay of L samples is produced compulsorily for a sampling frequency Fs as seen in FIG. 6C. Consequently, even if a digital filter is designed freely by the DSP/CPU, this component is inserted in series without fail as represented by an equivalent block in FIG. 6C. It is to be noted that, in applicable figures, the [sample] unit is described briefly as [smp].

Here, the L samples of the delay amount may not necessarily be an integer because the ADC/DAC or the like may use an oversampling technique. Further, strictly the DSP/CPU sometimes have a buffering structure for one to several samples when they form an input/output stream, and also the buffer has an influence as delay of the circuit. However, in the following description, it is assumed for the simplified description that the L samples of the delay amount are an integer and the delay amount generated in the DSP/CPU is included in the delay by the ADC/DAC.

For example, as a general example, if it is assumed that the delay amount generated in the inside of each of devices of the ADC and the DAC whose sampling frequency Fs is Fs=48 kHz is 20 samples for the sampling frequency Fs, then delay of totaling 40 samples is generated by the ADC and the DAC in the FB filter circuit 12 even if arithmetic operation relating to the DSP/CPU and so forth is not performed. As a result, the delay of 40 samples is applied as a delay of the open loop to the entire system.

Figure 7A:
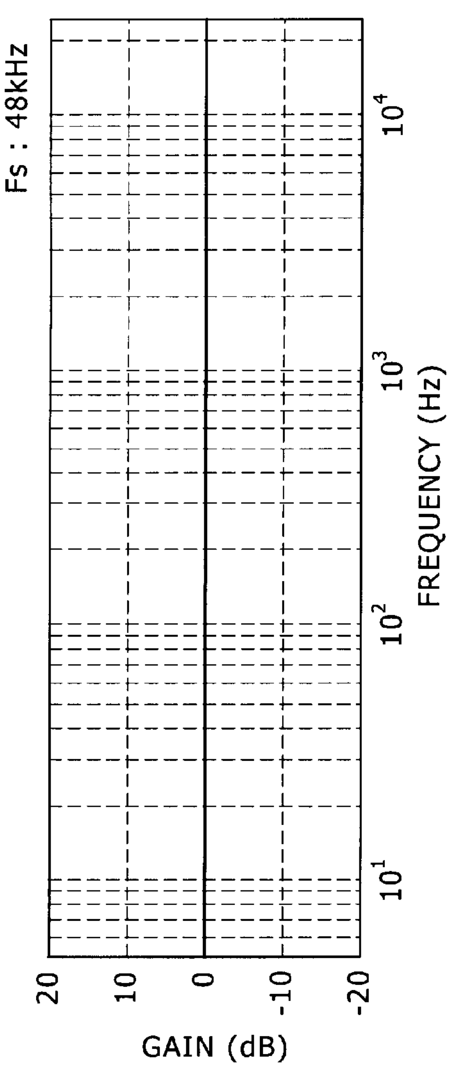
FIGS. 7A and 7B are diagrams illustrating a gain and a phase corresponding to a delay amount of 40 samples where the sampling frequency is 48 kHz.
Figure 7B:
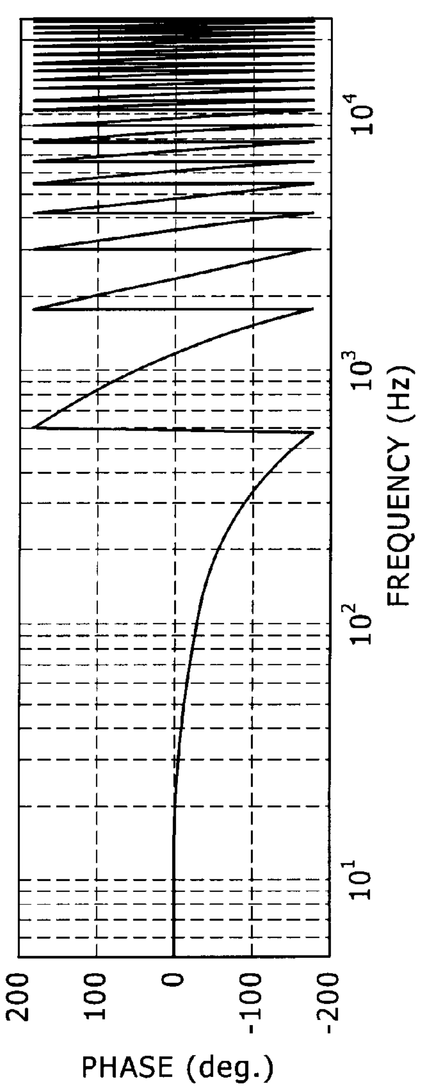
Figure 8A:
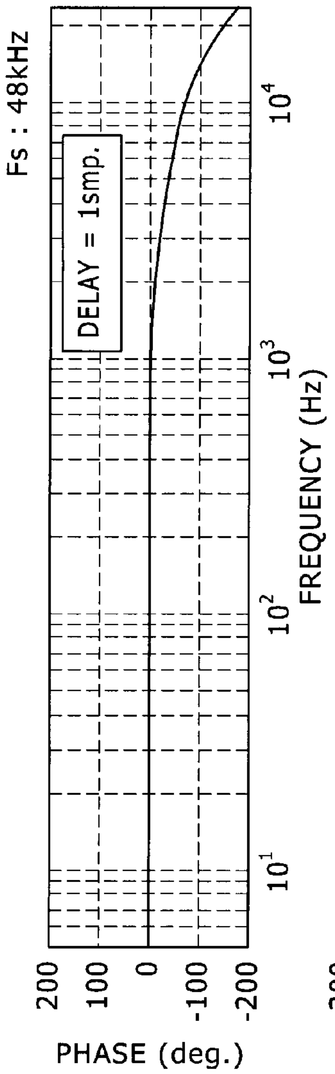
FIGS. 8A, 8B and 8C are diagrams illustrating the state of the phase where the sampling frequency is 48 kHz and the delay amount is one sample, two samples and three samples, respectively.
Figure 8B:
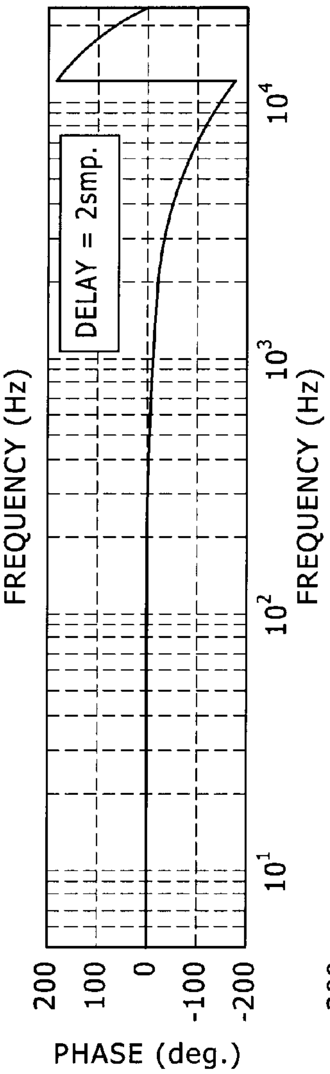
Figure 8C:
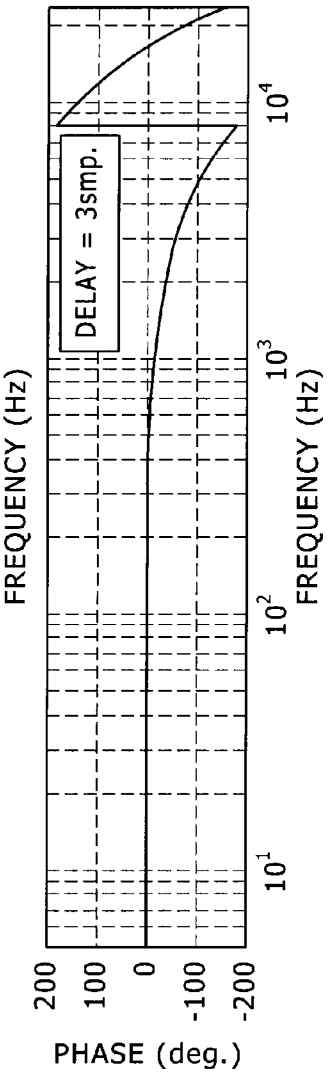
Figure 9A:
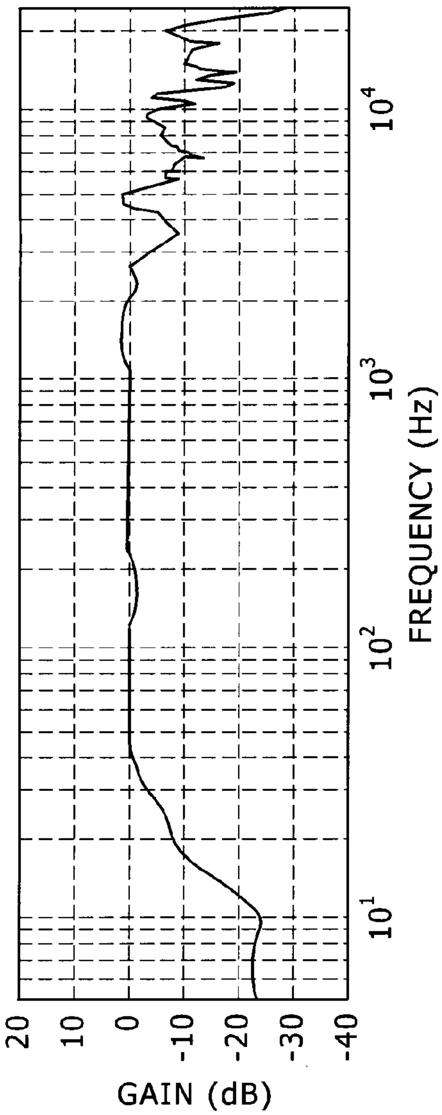
FIGS. 9A and 9B are diagrams illustrating measurement values of the transfer function from a driver to a microphone in the noise canceling system of the feedback type.

The delay amount involved in the FB filter circuit 12 is described more particularly using actual measurement values. FIGS. 7A and 7B illustrate a gain and a phase corresponding to the delay amount of 40 samples where the sampling frequency Fs is Fs=48 kHz. Meanwhile, FIGS. 8A to 8C illustrate the state of the phase where the delay amount is 1 sample, 2 samples and 3 samples, respectively, while the sampling frequency Fs is Fs=48 kHz. Further, FIGS. 9A and 9B illustrate measurement values of the transfer function from the driver to the microphone in the noise canceling system of the feedback type.

More particularly, in FIG. 7A, the axis of abscissa indicates the frequency, and the axis of ordinate indicates the gain. Meanwhile, in FIG. 7B, the axis of abscissa indicates the frequency, and the axis of ordinate indicates the phase. As seen from FIG. 7B, rotation of the phase starts from several tens Hz, and the phase rotates by a great amount until the frequency comes to Fs/2 (24 kHz), that is, to one half the sampling frequency Fs.

This can be recognized readily if it can be understand that the delay by one sample at the sampling frequency Fs=48 kHz corresponds to a phase delay by 180 degrees (π) at the Fs/2 frequency as seen in FIG. 8A and similarly the delays by two samples and three samples correspond to 360 degrees (27) and 540 degrees (3π) as seen from FIGS. 8B and 8C, respectively. In other words, in the example, as the delay amount increases by one sample, the phase delay increases by π.

Figure 9B:
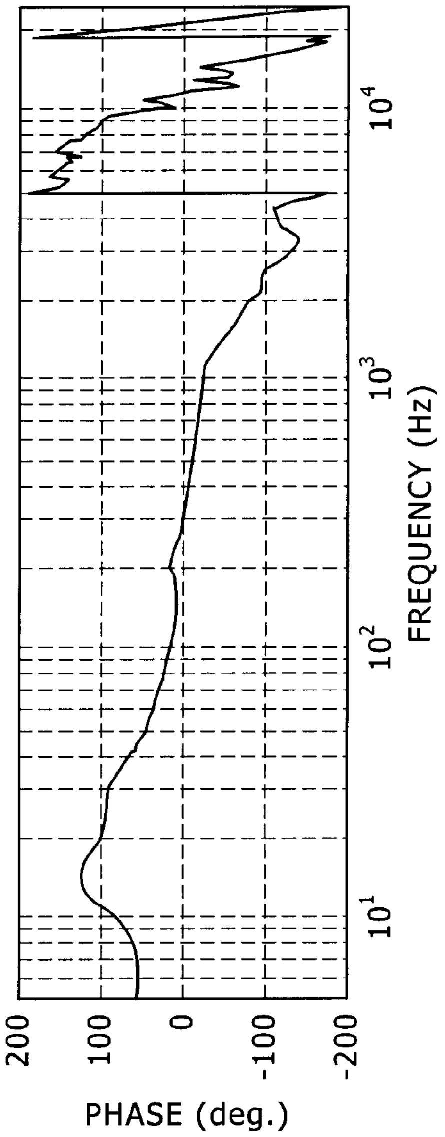

Meanwhile, in the noise canceling system of the feedback type, as seen also in FIG. 1A, since the position of the microphone 111 is set to a place in the proximity of the front face of the driver 15, the distance between them is small, and it can be recognized that the transfer function from the driver to the microphone exhibits a comparatively small amount of phase rotation as seen in FIG. 9B. This is apparent also from comparison between FIG. 7B and FIG. 9B.

The transfer function from the driver to the microphone in the noise canceling system of the feedback type whose characteristics are illustrated in FIGS. 9A and 9B corresponds to ADHM in the expressions (1) and (2) in FIG. 3, and a result of multiplication between this transfer function and the −β characteristic of the FB filter circuit 12 on the frequency axis as it is makes an open loop. The characteristic of this open loop must satisfy the two conditions including the condition (1) that, when the phase passes a point of 0 degree, the gain must be lower than 0 dB (0 decibel) and the condition (2) that, when the gain is higher than 0 dB, the phase must not include a point of 0 degree.

If the phase characteristic of FIG. 7B is examined again here, then it can be seen that the phase rotates one rotation ($2\pi$) in the proximity of 1 kHz after it stars from 0 degree. In addition, also in the ADHM characteristic of FIG. 9B (in the transfer characteristic from the driver to the microphone), phase delay exists depending upon the distance from the driver to the microphone.

If the block diagram or structure diagram shown in FIG. 6C which represents the FB filter circuit 12 functionally is examined, then while the filter section 122 (implemented using a DSP/CPU) which can be designed freely is connected in series to the delay component by the DSP/CPU, it is basically difficult to design a filter having a leading phase in the digital filter section 122 from the law of casualty. However, depending upon the configuration of the filter shape, it may be possible to compensate for a "partial" phase lead only within a particular frequency band. However, it is impossible to form such a phase leading circuit over a wide frequency band which compensates for phase rotation by the delay component by the ADC/DAC.

From this, it can be recognized that, even if a preferable digital filter is designed by the DSP/CPU 122 in the FB filter circuit 12 (−β block), the frequency band within which a noise reduction effect can be obtained from the feedback configuration in this instance is limited to less than approximately 1 kHz at which the phase rotates by one rotation, and if an open loop which incorporates also the ADHM characteristic is assumed and a phase margin and a gain margin are taken into account, then the attenuation amount and the attenuation frequency band are further narrowed.

Figure 10A:
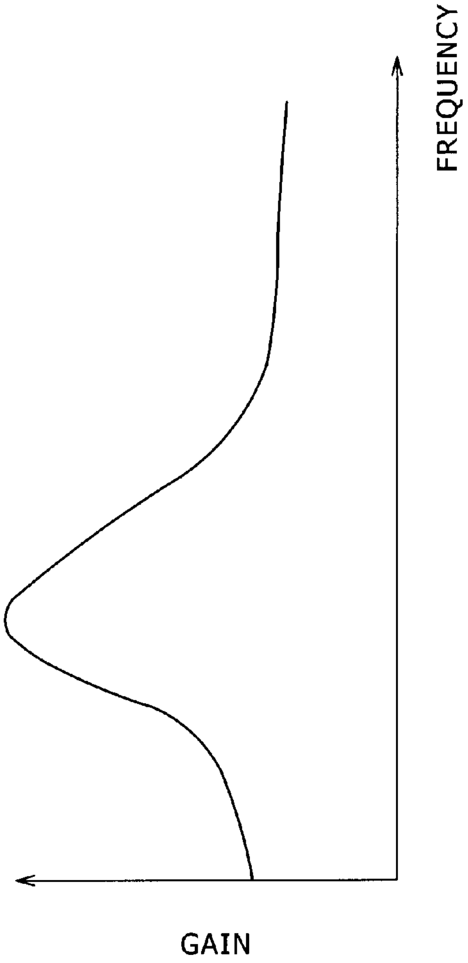
FIGS. 10A and 10B are diagrams illustrating desirable gain and phase characteristic of the FB filter circuit.
Figure 10B:
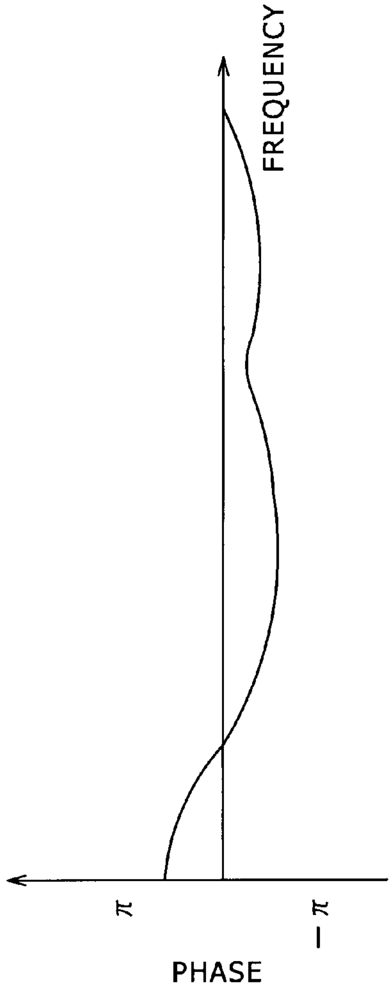

FIGS. 10A and 10B illustrate desirable characteristics of the FB filter circuit 12. In particular, FIG. 10A illustrates a desirable gain characteristic, and FIG. 10B illustrates a desirable phase characteristic. It can be recognized that the desirable characteristics of the FB filter circuit 12 (β characteristic (phase inverting system in the FB filter circuit 12)) with respect to such characteristics as illustrated in FIGS. 9A and 9B have such a shape that, while the gain shape has a substantially mountain-like shape over a frequency range within which a noise reduction effect is intended as seen in FIG. 10A, the phase rotation does not occur very much as seen in FIG. 10B. In particular, in FIG. 10B, the phase characteristic does not exhibit one rotation within a range from a low frequency region to a high frequency region.

However, in such a configuration as shown in FIGS. 6B and 6C, to form an FB filter circuit (β filter shape) having such characteristics as seen in FIGS. 10A and 10B using digital filters connected in series to obtain such a delay characteristic having many phase rotations as seen in FIG. 7B requires recovery of the phase by a great amount and is impossible. Thus, it is a current object to produce a shape with which the phase does not make one rotation because, if the phase rotates one rotation within an FB filter (β filter) (or FB filter circuit (−β block)), then the noise attenuation characteristic is damaged significantly also from the shape limitation of FIG. 4.

It is to be noted that, if the phase rotation is small within an object frequency band (principally within a low frequency region) of the noise reduction, essentially the phase variation outside the frequency band has no relation (only if the gain drops). However, if the amount of the phase rotation in a high frequency region is great, then this generally has not a little influence on a low frequency region, and therefore, the present invention is directed reduction of the phase rotation over a wide frequency band in design. In this significance, it is not preferable for the noise reduction effect to be reduced significantly when compared with that where analog circuits are used in system design in exchange for the merits by the digitalized formation described hereinabove.

[Particular Configuration and Operation of the Invention]

According to the present invention, the above-described merits achieved by digitalized formation of the FB filter circuit 12 and the FF filter circuit 22 are made the most of while it is made possible to reduce the delay in the FB filter circuit 12 and the FF filter circuit 22 to keep a high noise reduction effect.

It is to be noted that, while the present invention can be applied not only to a noise canceling system of the feedback type but also to a noise canceling system of the feedforward type, the following description is given taking a case wherein the present invention is applied to a noise canceling system of the feedback type as an example in order to simplify the description.

Figure 11A:
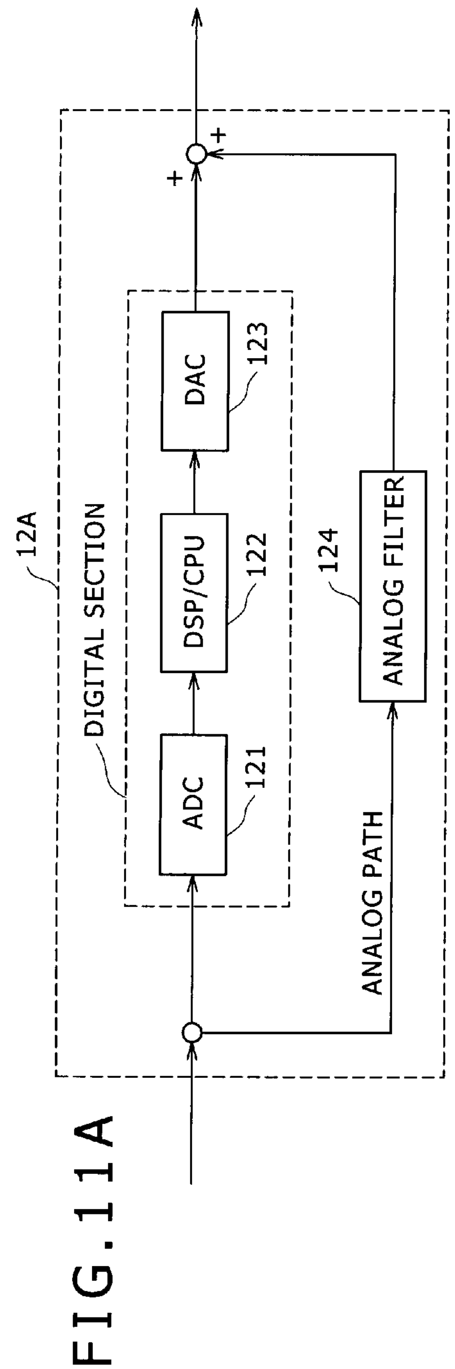
FIGS. 11A and 11B are block diagrams showing an example of a configuration of an FB filter circuit according to the present invention.
Figure 11B:
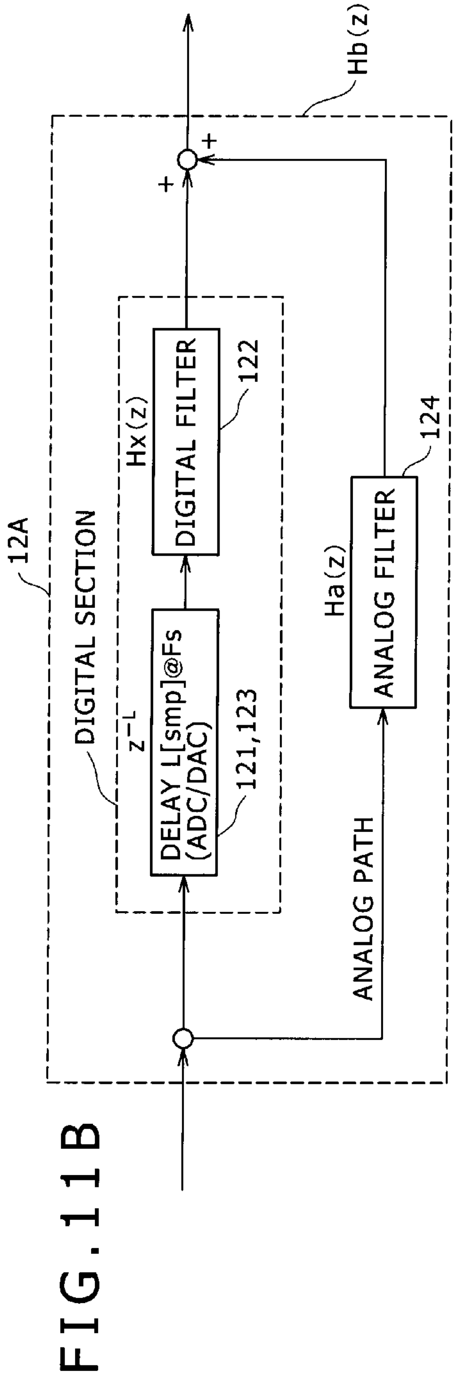

FIGS. 11A and 11B show an example of a configuration of an FB filter circuit according the present invention. The FB filter circuit 12A here is not designed such that it is replaced only by digital elements including an ADC/DAC as seen in FIG. 6B. In particular, the new FB filter circuit 12A (−β block) is configured such that an analog path including an analog filter 124 is additionally provided in parallel to a digital section which includes an ADC 121, a DSP/CPU 122 and a DAC 123 such that output signals from the digital section and the analog path can be added as analog signals as seen in FIG. 11A.

The FB filter circuit 12A having the configuration described above with reference to FIG. 11A can be represented in such a manner that it includes, as seen in FIG. 11B, ADC/DAC section 121, 123 which generates delay L, and a digital filter section 122 formed from a DSP/CPU. Also in FIG. 11B, a delay by L samples is generated compulsorily for the sampling frequency Fs by the ADC/DAC section 121, 123 and is indicated as "delay L[smp]@Fs] similarly as in FIG. 6C.

While the FB filter circuit 12A shown in FIGS. 11A and 11B is configured such that an output of the analog filter 124 in the form of an analog signal and an output of the digital filter section 122 in the form of an analog signal are added by a mixer section (synthesis section), the configuration of the FB filter circuit 12A is not limited to this. FIGS. 13A and 13B show another example of the FB filter circuit according to the present invention.

The FB filter circuit 12B shown in FIG. 13A is configured such that it does not include the analog filter 124 while, to an output (analog signal) of a digital section which includes an ADC 121, a DSP/CPU 122 and a DAC 123, an analog signal inputted to the digital section can be added. The FB filter circuit 12B having the configuration just described with reference to FIG. 13A can be represented in such a manner as seen in FIG. 13B wherein it is composed of an ADC/DAC section 121, 123 formed from the ADC/DAC which generates a delay of L samples and a digital filter section 122 formed from a DSP/CPU.

It can be interpreted that the FB filter circuit 12B shown in FIGS. 13A and 13B is a special form of the FB filter circuit 12A shown in FIGS. 11A and 11B. However, the FB filter circuit 12B shown in FIGS. 13A and 13B assures high reliability as a system in terms of the dispersion and the stability because it has no analog filter and hence has no analog terminals.

Then, the FB filter circuit 12B is designed so that a signal obtained by adding an analog signal processed by the analog filter 124 after processing by the analog filter 124 shown in FIGS. 11A and 11B or the analog path having a through-characteristic shown in FIGS. 13A and 13B is performed in parallel to processing by the digital filter or an analog signal processed by an analog path which indicates a through-characteristic to a signal processed by the digital section (digital filter) may have such filter characteristics as seen in FIGS. 10A and 10 as β characteristics. While it is generally possible to alter an analog filter circuit, this increases the system scale. On the other hand, alteration of a digital filter can be performed readily by software on a DSP/CPU.

Therefore, in order to use the FB filter circuit 12A shown in FIGS. 11A and 11B or the FB filter circuit 12B shown in FIGS. 13A and 13B to incorporate a plurality of modes having different noise reduction effects, it is an efficient technique to fix an analog filter or a through analog path as it is while a plurality of digital filters are designed and selectively used as occasion demands. This technique is used in the FB filter circuits according to the embodiment of the present invention.

Figure 14:
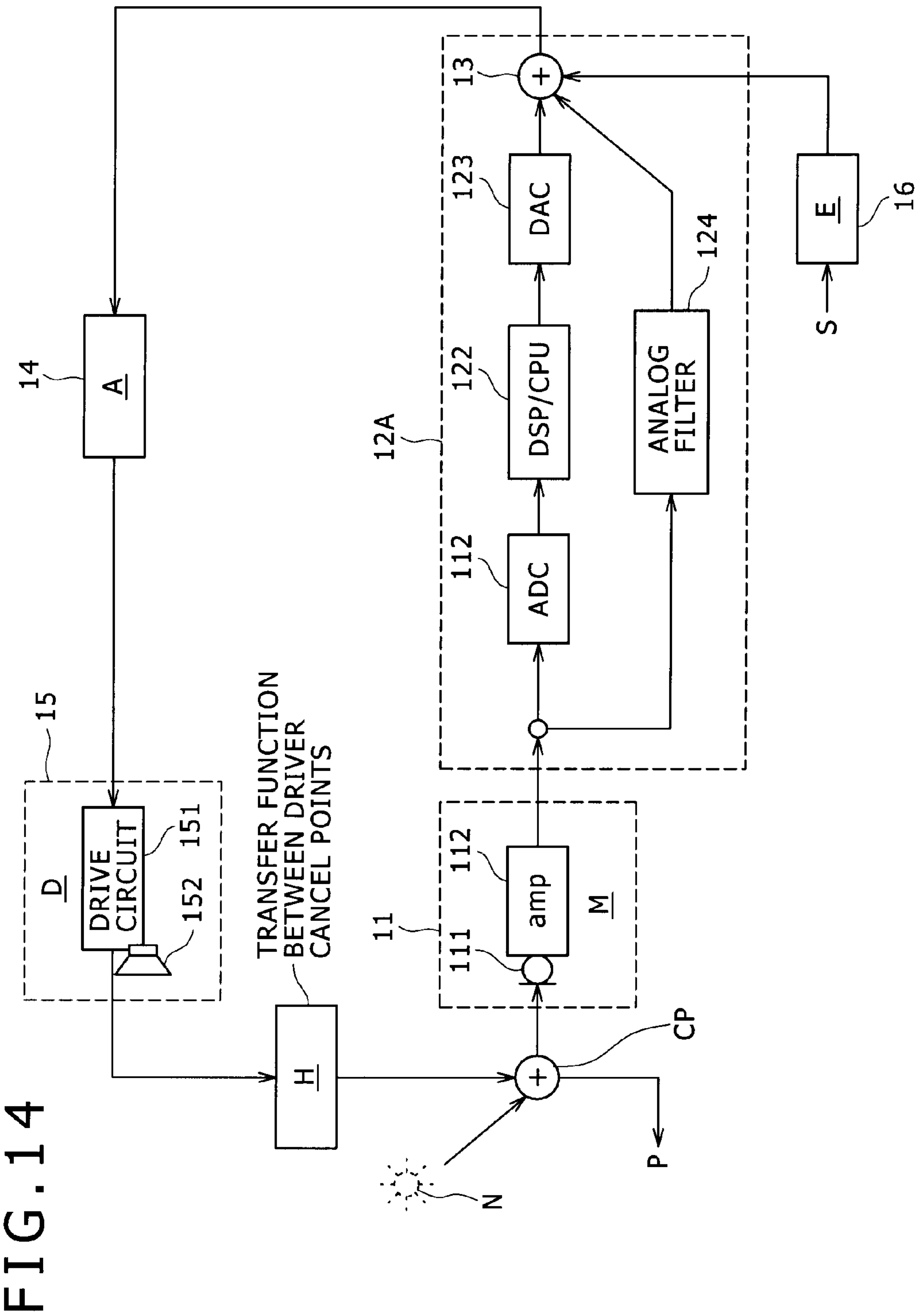
FIGS. 14 and 15 are block diagrams showing configurations of different noise canceling systems of the feedback type to which different forms of the FB filter circuit according to the present invention are applied.
Figure 15:
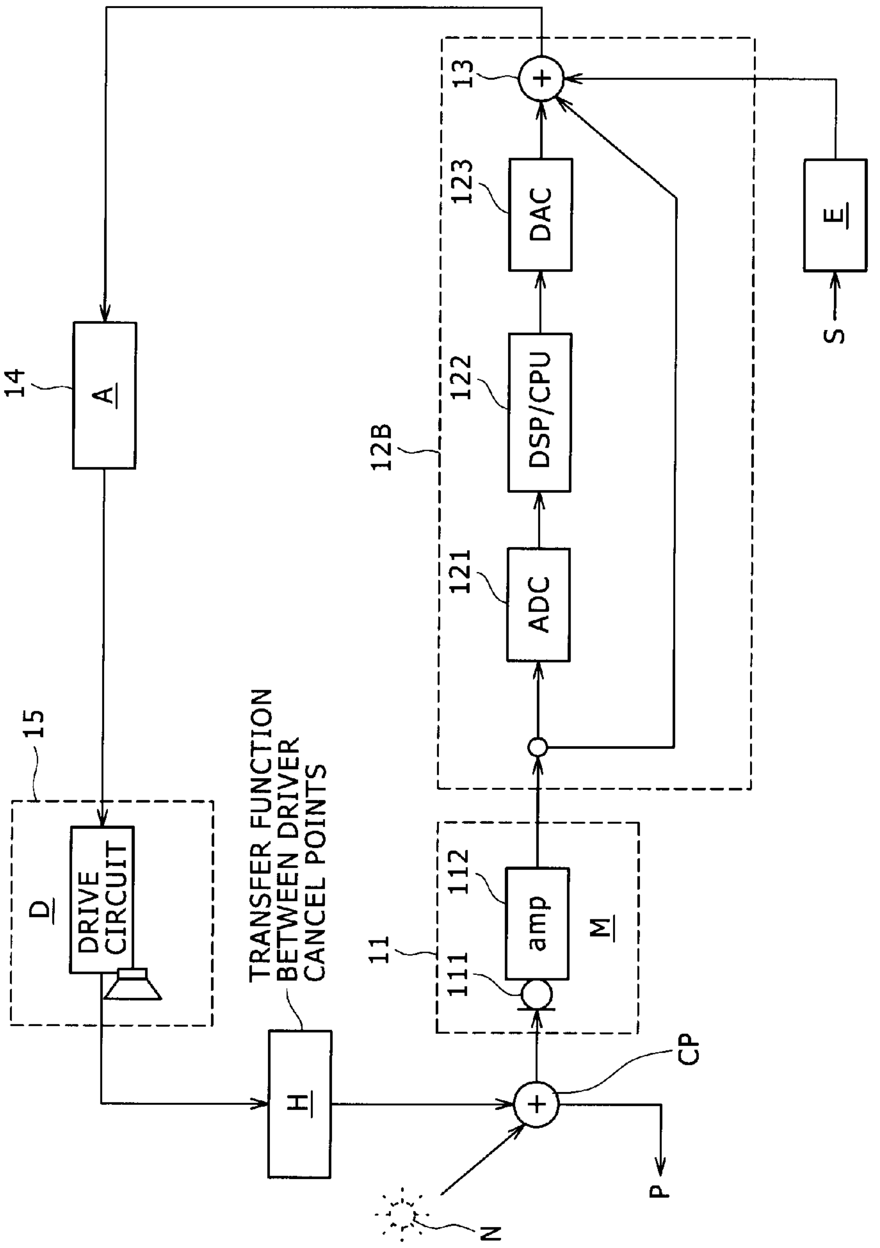

Each of FIGS. 14 and 15 shows a configuration of an entire noise canceling system of the feedback type where an FB filter circuit according to the present invention is applied to the system. In particular, FIG. 14 shows a noise canceling system of the feedback type wherein the FB filter circuit 12A having the configuration shown in FIGS. 11A and 11B, that is, the FB filter circuit 12A including the digital section composed of the ADC 121, DSP/CPU 122 and DAC 123 and the analog filter 124 connected in parallel to the digital section, is interposed between the microphone and microphone amplification section 11 and the power amplifier 14.

Meanwhile, FIG. 15 shows another noise canceling system of the feedback type wherein the FB filter circuit 12B having the configuration shown in FIGS. 13A and 13B, that is, the FB filter circuit 12B including the digital section composed of the ADC 121, DSP/CPU 122 and DAC 123 and the analog path having a through-characteristic and connected in parallel to the digital section, is interposed between the microphone and microphone amplification section 11 and the power amplifier 14.

As seen in FIGS. 14 and 15, the FB filter circuit 12A having the configuration shown in FIGS. 11A and 11B and the FB filter circuit 12B having the configuration shown in FIGS. 13A and 13B can be used as an FB filter circuit of a noise canceling system of the feedback type.

FIG. 12 shows calculation expressions for a characteristic Hb(z) of the FB filter circuit 12A shown in FIG. 11B and a characteristic Hx(z) of the digital filter section (DSP/CPU) 122 shown in FIG. 11B.

Referring to FIG. 11B, if the characteristic of the analog filter 124 is represented by Ha(z), the characteristic of the digital filter section 122 by Hx(z) and the β characteristic (design target characteristic, that is, the characteristic of the FB filter circuit 12A) by Hb(z), then the characteristic Hb(z) can be represented by an expression which uses z conversion like an expression (1) in FIG. 12.

It is to be noted that the characteristics Ha(z) and Hb(z) are defined by characteristics originally in an analog region, and also actual addition is performed in an analog mode. Here, however, in order to facilitate calculation, the Ha(z) and Hb(z) characteristics are handled in a form wherein they are discretized with the sampling frequency Fs in a digital region in FIGS. 11A, 11B and 12.

Then, if the expression (1) in FIG. 12 is transformed into an expression for the determination of the characteristic Hx(z) of the digital filter section 122, then such an expression (2) as in FIG. 12 is obtained. In the expression (2) of FIG. 12, since the part of the +Lth power to Z which is a coefficient part (part of $Z^{+L}$) signifies a time lead by L samples, in order for the digital filter Hx(z) to satisfy the law of casualty, the difference (Hb(z)−Ha(z)) in impulse response between the target characteristic Hb(z) and the analog filter Ha(z) must exhibit coincidence within a period of time of L samples from the top on the time axis. If they do not exhibit coincidence in response within the period of time of L samples, then the characteristic Hx(z) comes to have a coefficient to negative time, and it is actually impossible to construct a filter.

In the following, a noise canceling system to which the FB filter circuit according to the present invention is applied is described in detail taking a noise canceling system of the feedback type which uses the FB filter circuit 12B having the configuration shown in FIGS. 13A and 13B which includes a digital filter whose sampling frequency Fs is Fs=96 kHz and wherein the delay by the ADC/DAC section is 26 samples and an analog path having a through-characteristic and connected in parallel to the digital filter as an example.

Figure 16A:
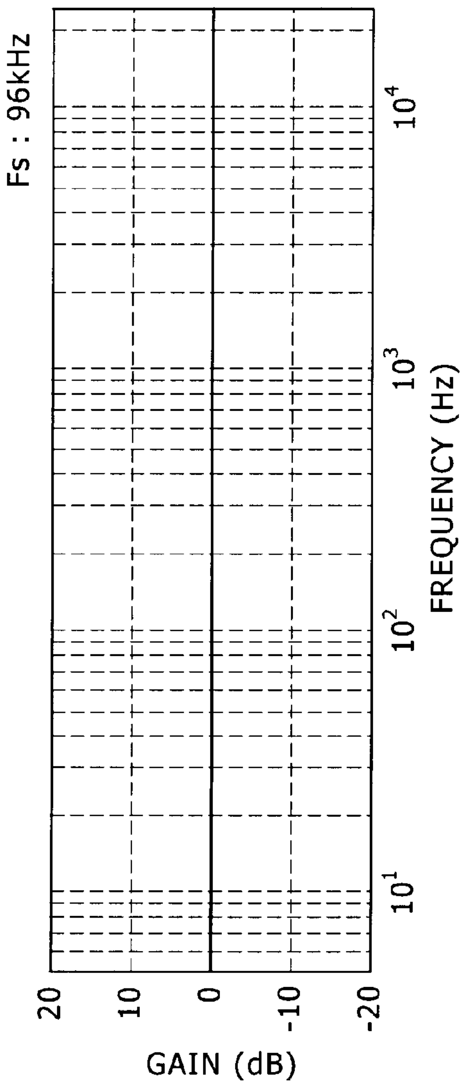
FIGS. 16A and 16B are diagrams illustrating a gain and a phase, respectively, of a delay characteristic of ADC/DAC sections shown in FIGS. 14 and 15.
Figure 16B:
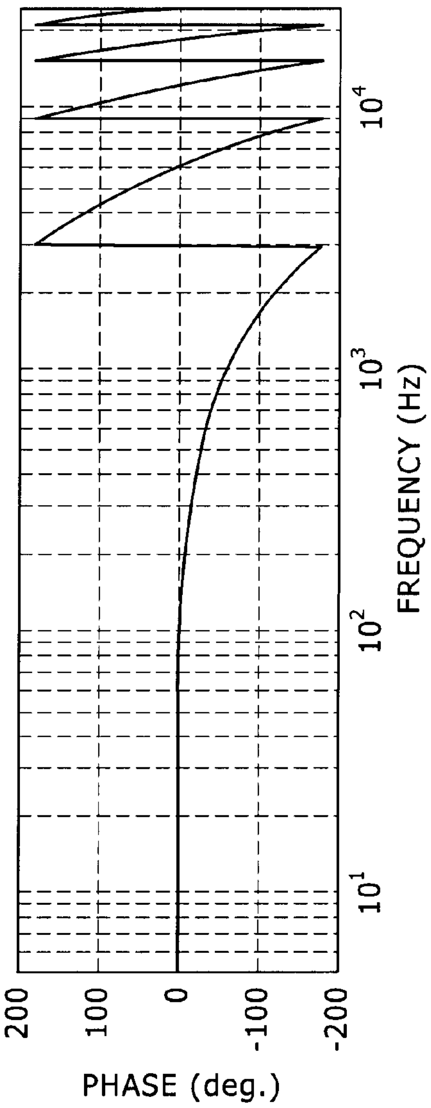

FIGS. 16A and 16B illustrate the gain and the phase of the delay characteristics of the ADC/DAC 121 and 123 in the present example. In particular, in FIG. 16A, the axis of abscissa indicates the frequency and the axis of ordinate indicates the gain. Meanwhile, in FIG. 16B, the axis of abscissa indicates the frequency and the axis of ordinate indicates the phase. As can be recognized from comparison between the characteristics of FIGS. 16A and 16B and the characteristics of the gain and the phase corresponding to the delay amount of 40 samples in the case of the sampling frequency Fs=48 kHz illustrated in FIGS. 7A and 7B, the sampling frequency Fs is higher and the filer delay is smaller with the characteristics illustrated in FIGS. 16A and 16B than with the characteristics illustrated in FIG. 7. Therefore, the phase rotates one rotation in 6 kHz, and the phase margin increases with regard to the β characteristic which makes a noise attenuation effect.

However, even with such ADC/DAC delay characteristics as seen in FIGS. 16A and 16B, if such a β characteristic block as seen in FIGS. 6A to 6C is replaced directly by a digital filer, then the bandwidth within which the noise reduction effect can be anticipated becomes narrower than that where an analog filter is used and the noise reduction effect becomes lower.

In order to make the most of the merits by digitalized formation (such as mode changeover and so forth) while the frequency band and effect of noise attenuation are expanded, the technique described above with reference to FIGS. 11A, 11B, 13A and 13B (the technique is hereinafter referred to as hybrid feedback system) is applied. Examples of a configuration and characteristics of such FB filter circuits are described with reference to FIGS. 17 to 22B.

[Particular Examples of the FB Filter Circuit of the Hybrid Feedback Type]

[Particular Example 1 of the FB Filter Circuit of the Hybrid Feedback Type]

Figure 17:
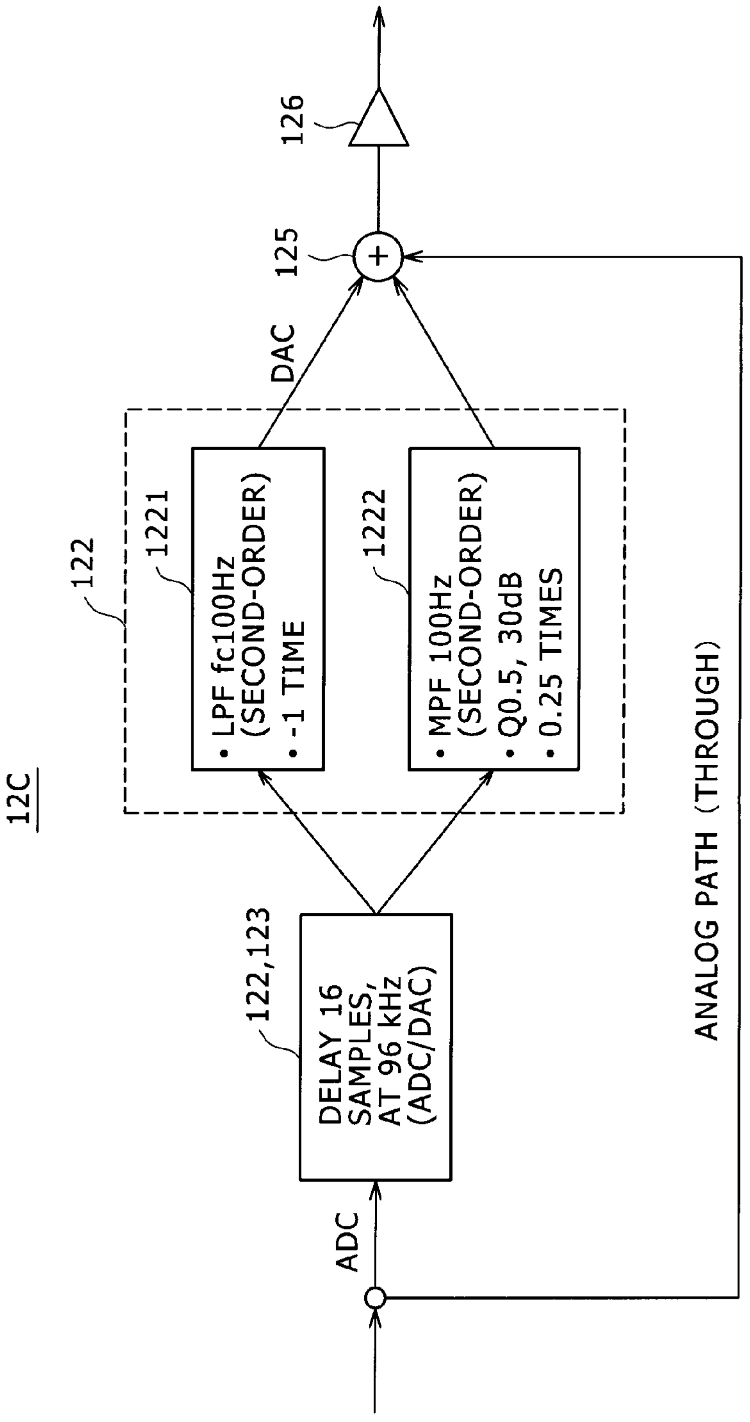
FIG. 17 is a block diagram showing an example of a particular configuration of the FB filter circuit.

FIG. 17 shows an FB filter circuit 12C as an example, that is, a particular example 1, of a configuration of the FB filter circuit. Referring to FIG. 17, the FB filter circuit 12C is configured such that an analog path is designed as a through-path without using an analog filter while a digital filter section 122 is formed from a parallel circuit of a low-pass filter (LPF) 1221 and a mid presence filter (MPF) 1222 formed from a digital second-order IIR (Indefinite Impulse Response) filter. In other words, the FB filter circuit 12C shown in FIG. 17 is one of examples of a particular configuration of the FB filter circuit 12B shown in FIGS. 13A and 13B.

It is to be noted that, while, also in FIG. 17, the ADC 121 and the DAC 123 as a section for generating delay are shown as a single block, actually an output of the LPF 1221 and an output of the MPF 1222 which form the digital filter section 122 are converted into analog signals by the DAC 123 and then synthesized also in a form wherein an analog signal from the analog path is added by a synthesis section 125. The signal synthesized by the synthesis section 125 is supplied to an inverter 126, by which it is processed so as to have an inverted phase, and the signal after the processing is outputted.

Figure 18:
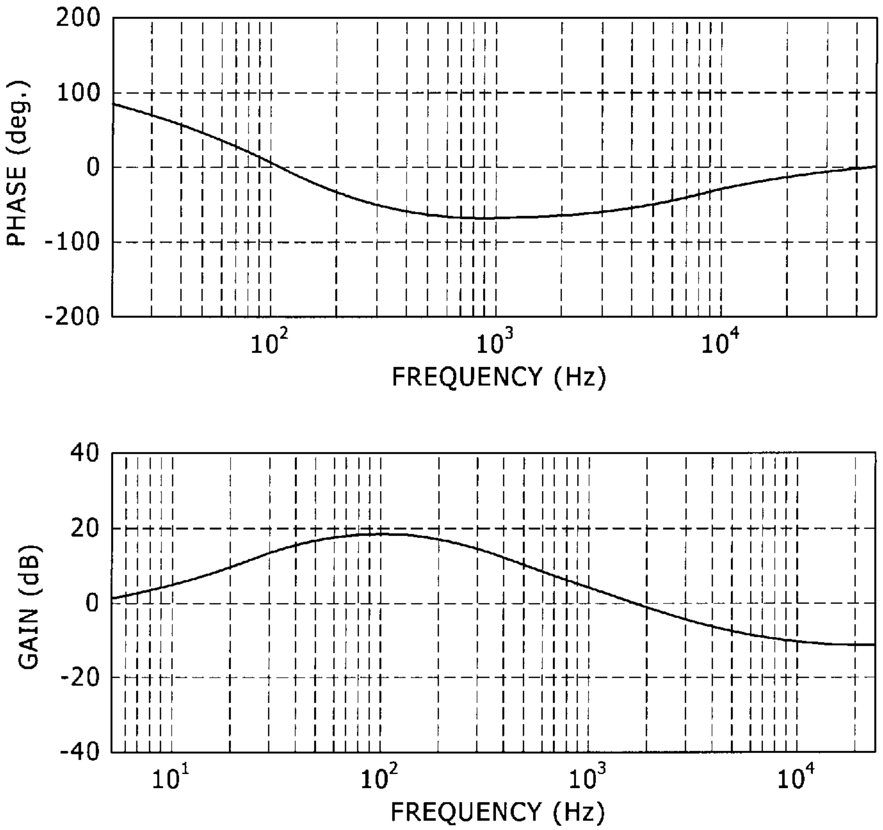
FIG. 18 is a diagram illustrating characteristics only of a digital filter section, that is, a parallel circuit of an LPF and an MPF, of the FB filter circuit shown in FIG. 17.
Figure 19A:
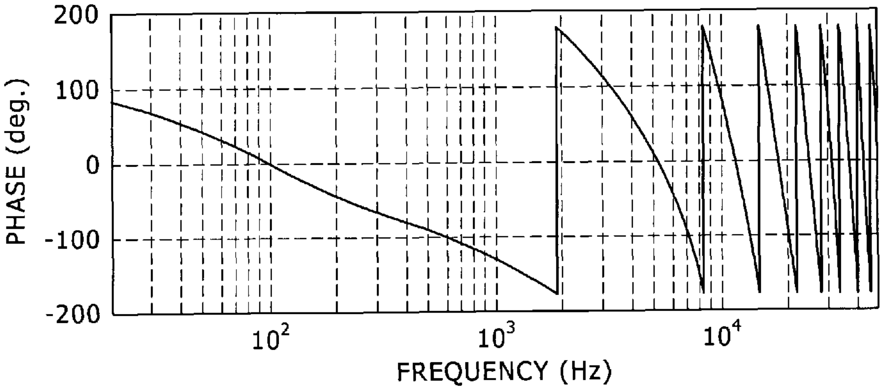
FIGS. 19A and 19B are diagrams illustrating phase and gain characteristics of the digital filter section and an ADC/DAC section of the FB filter circuit shown in FIG. 17, respectively.
Figure 19B:
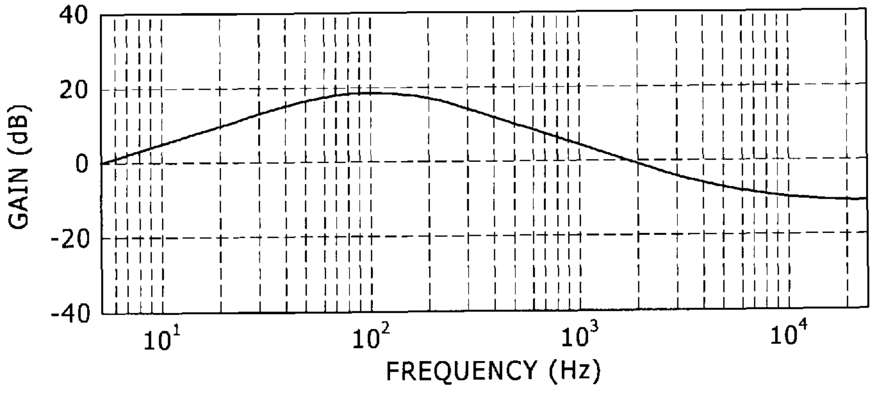

FIG. 18 illustrates characteristics only of the digital filter section (parallel circuit of the LPF and the MPF) 122 from within the FB filter circuit 12C shown in FIG. 17. Meanwhile, FIG. 19 illustrates characteristics where a delay of 16 samples by the ADC/DAC section 121, 123 is included in addition to that of the digital filter section 122. In FIGS. 18 and 19, the upper stage shows a graph of the phase characteristic wherein the axis of abscissa indicates the frequency and the axis of ordinate indicates the phase while the lower stage shows a graph of the gain characteristic wherein the axis of abscissa indicates the frequency and the axis of ordinate indicates the gain.

As can be recognized from comparison between FIGS. 18 and 19, the graphs on the upper stage exhibit a difference. In particular, if the delay characteristic of the ADC/DAC section is added to the characteristic of the digital filter section 122, that is, if the delay of 16 samples by the ADC/DAC is included, then although the gain characteristic exhibits no difference, the phase characteristic exhibits a difference. In other words, the gain characteristic involves phase rotation.

Figure 20A:
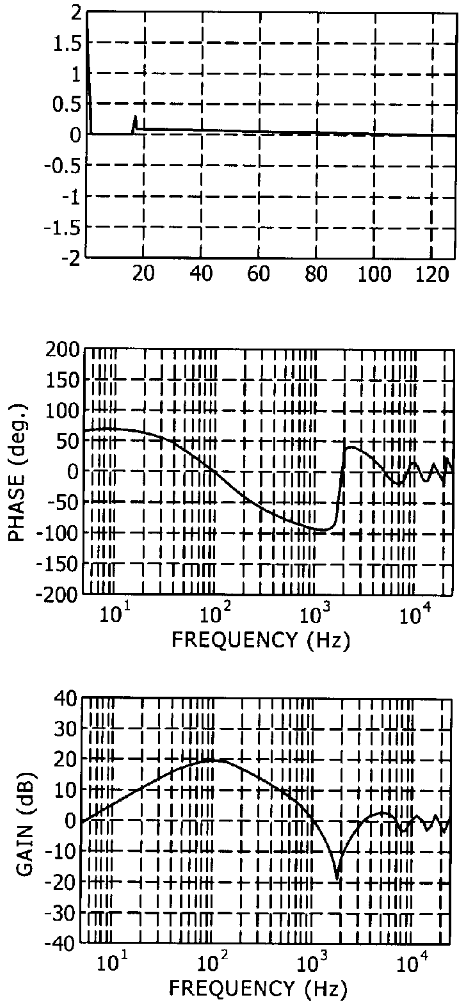
FIGS. 20A and 20B are diagrams illustrating β characteristics of the FB filter circuit shown in FIG. 17 and ADHM β characteristics of the FB filter circuit obtained by multiplying the β characteristics and actual measurement characteristics of the transfer function (ADHM)

The characteristic (β characteristic) of the FB filter circuit 12C shown in FIG. 17 which includes the digital section composed of the digital filter section 122 and the ADC/DAC section 121, 123 described hereinabove with reference to FIGS. 18 and 19 and the analog path having a through-characteristic is illustrated in FIG. 20A. Referring to FIG. 20A, the graph on the uppermost stage is a graph of a top portion (128 samples) of the pulse response of the transfer function where the axis of abscissa indicates the sample number and the axis of ordinate indicates the level. The graph on the middle stage is a graph of the phase characteristic where the axis of abscissa indicates the frequency and the axis of ordinate indicates the phase. The graph on the lowermost stage is a graph of the gain characteristic where the axis of abscissa indicates the frequency and the axis of ordinate indicates the gain.

As can be seen from FIG. 20A, the phase rotation is suppressed by addition of the analog path, and the phase does not rotate by one rotation over a range from a low frequency region to a high frequency region. Where the characteristics are viewed from another phase, the low frequency characteristic which becomes the center of noise reduction is influenced much by the digital filter section 122, but in the middle and high frequency regions within which the phase rotation is likely to increase by delay of the ADC/DAC section, the characteristic of the analog path which indicates a quick response is used effectively.

Figure 20B:
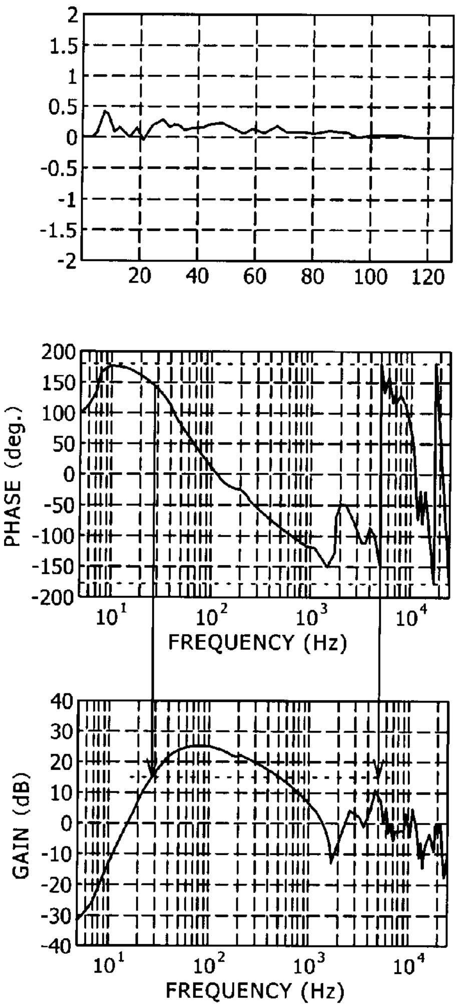

Graphs of characteristics (ADHMβ) obtained by multiplication of the characteristics illustrated in FIG. 20A, that is, the characteristics of the FB filter circuit 12 shown in FIG. 17 (β characteristics), and actual measurement characteristics of the transfer function (ADHM) illustrated in FIGS. 9A and 9B are illustrated in FIG. 20B. Also in FIG. 20B, similarly as in FIG. 20A, the graph on the uppermost stage is a graph of a top portion (128 samples) of the pulse response of the transfer function where the axis of abscissa indicates the sample number and the axis of ordinate indicates the level. The graph on the middle stage is a graph of the phase characteristic where the axis of abscissa indicates the frequency and the axis of ordinate indicates the phase. The graph on the lowermost stage is a graph of the gain characteristic where the axis of abscissa indicates the frequency and the axis of ordinate indicates the gain.

Then, the graph of the transfer characteristics (ADHMβ) shown in FIG. 20B is that of a system wherein the phase of the open loop (−ADHMβ) is inverted (multiplied by −1). If this system is considered as a system wherein the phase of the FB filter circuit 12 shown in FIGS. 6A to 6C is inverted, then oscillation occurs at a point of −π (−180 degrees) or π (180 degrees). Therefore, in the proximity of this phase point, it is necessary for the gain side characteristic to be lower than 0 dB.

Therefore, if the phase margin for prevention of loop oscillation is 30 degrees (the effective range of the phase is from −150 degrees to 150 degrees) as seen from the graph on the middle stage and the axis of ordinate of the gain is regarded as a relative value, then the characteristic (β characteristic) of the FB filter circuit can be actually shifted on the graph shown on the lowermost stage of FIG. 20B until a horizontal broken line indicated by a thick line comes to new 0 dB. In this instance, approximately 13 dB in the maximum contributes to the feedback loop. It is to be noted that, while a phase margin exists on both of the low frequency side and the high frequency side from the shape of the mountain, naturally the gain is adjusted to that one of the gain up limits at which oscillation is less likely to occur.

[Particular Example 2 of the FB Filter Circuit of the Hybrid Feedback Type]

Figure 21:
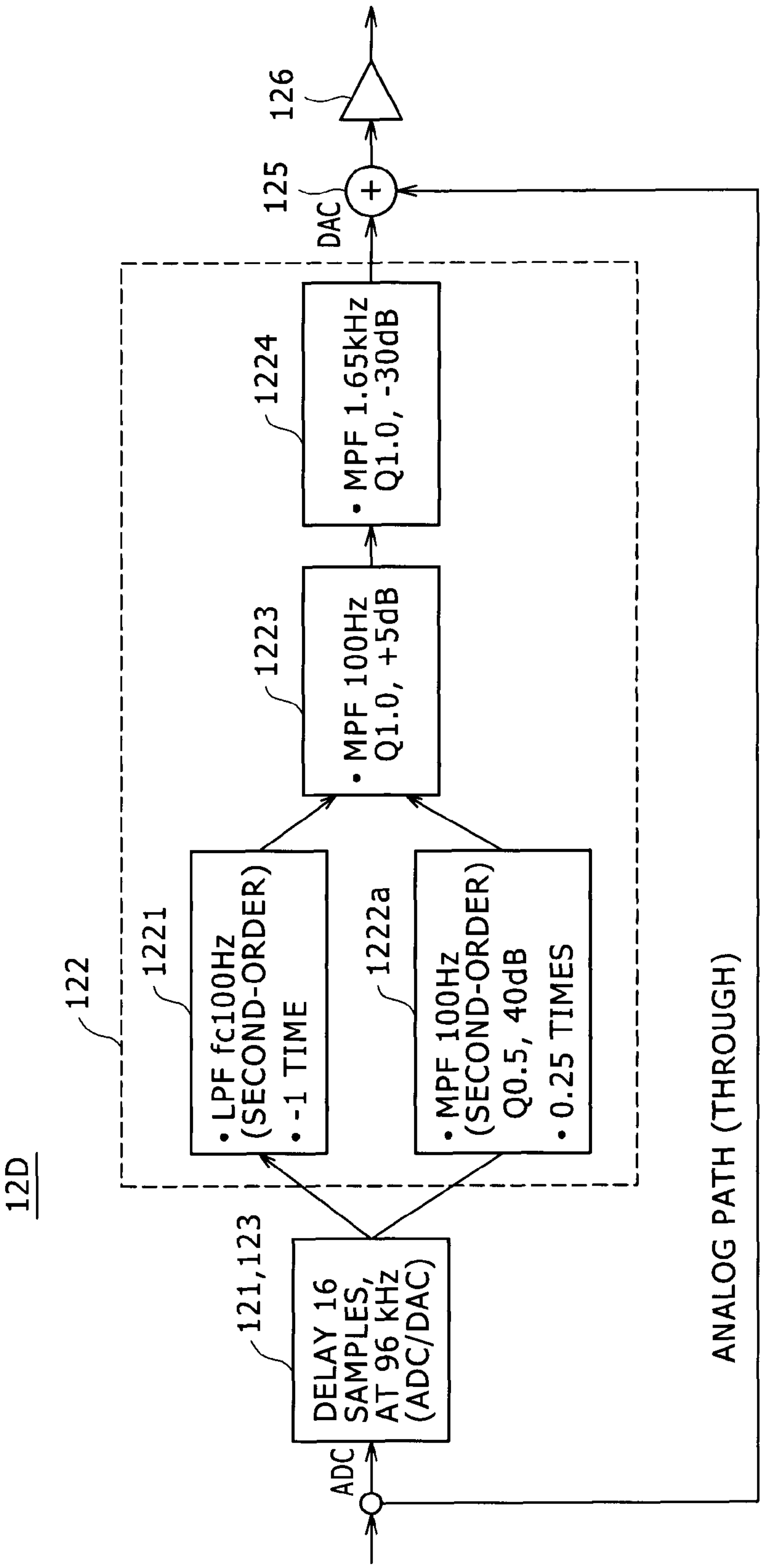
FIG. 21 is a block diagram showing another particular example of the configuration of the FB filter circuit.

FIG. 21 shows an FB filter circuit 12D as another example, that is, a particular example 2, of the configuration of the FB filter circuit. Referring to FIG. 21, also the FB filter circuit 12D is configured such that an analog path is designed as a through-path without using an analog filter. Further, the FB filter circuit 12D shown in FIG. 21 is produced such that an MPF 1223 and another MPF 1224 which have a configuration of an IIR filter are provided at a stage next to an LPF 1221 and an MPF 122*sa* which have a configuration of a digital second-order IIR filter and are provided in parallel, respectively, intending to increase the attenuation amount although the bandwidth is narrow.

In particular, while the FB filter circuit 12C of the configuration shown in FIG. 17 is for a comparatively wide bandwidth, the FB filter circuit 12D of the configuration shown in FIG. 21 exhibits a great attenuation amount although the bandwidth is narrow. It is to be noted that also the FB filter circuit 12D of the configuration shown in FIG. 21 has an analog path of a through-characteristic and is one of particular examples of the configuration of the FB filter circuit 12B shown in FIG. 13.

Also in the case of the FB filter circuit 12D shown in FIG. 21, the ADC 121 and the DAC 123 are represented by one block as a section for generating delay, and an output from the MPF 1224 is converted into an analog signal by the DAC 123 and then synthesized with an analog signal from the analog path by the synthesis section 125. The signal synthesized by the synthesis section 125 is supplied to the inverter 126, by which it is processed so that the phase thereof is inverted, whereafter it is outputted.

Figure 22A:
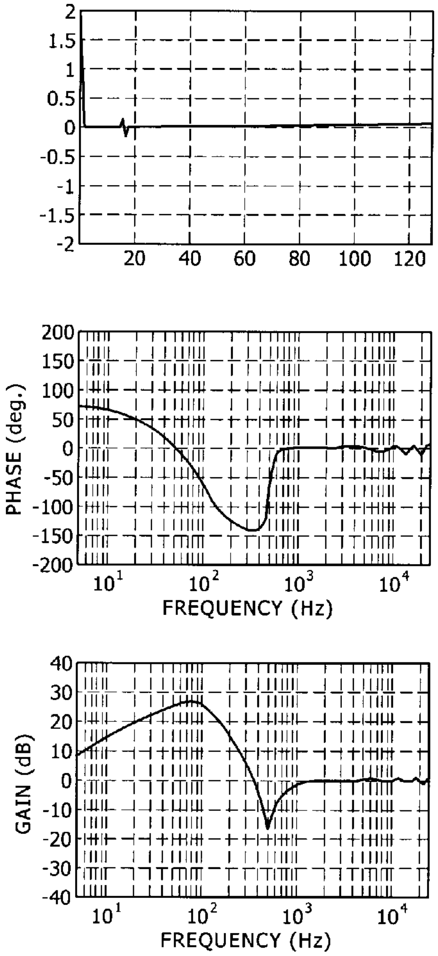
FIGS. 22A and 22B are diagrams illustrating β characteristics of the FB filter circuit shown in FIG. 21 and ADHM β characteristics of the FB filter circuit obtained by multiplying the β characteristics and actual measurement characteristics of the transfer function (ADHM)

FIG. 22A illustrates characteristics (β characteristics) of the FB filter circuit 12D of the configuration shown in FIG. 21 while the analog path is fixed. Meanwhile, FIG. 22B is a graph of a characteristics (ADHMβ) obtained by multiplication of the characteristics illustrated in FIG. 22A, that is, the characteristics (β characteristics) of the FB filter circuit 12D shown in FIG. 21, and actual measurement characteristics of the transfer function (ADHM) illustrated in FIGS. 9A and 9B on the frequency axis.

Figure 22B:
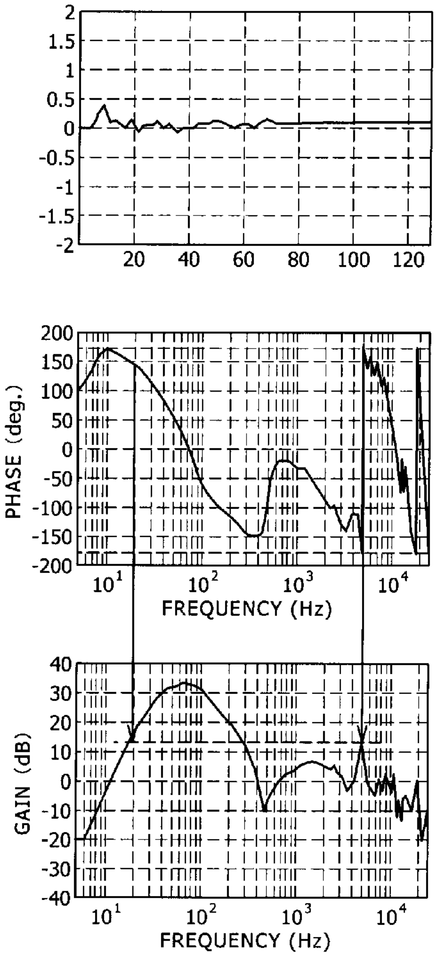

In each of FIGS. 22A and 22B, the graph on the uppermost stage is a graph of a top portion (128 samples) of the pulse response of the transfer function where the axis of abscissa indicates the sample number and the axis of ordinate indicates the level. The graph on the middle stage is a graph of the phase characteristic where the axis of abscissa indicates the frequency and the axis of ordinate indicates the phase. The graph on the lowermost stage is a graph of the gain characteristic where the axis of abscissa indicates the frequency and the axis of ordinate indicates the gain.

Also in the case of FIG. 22A, the phase rotation is suppressed by addition of the analog path similarly as in the case of FIG. 20A described hereinabove, and the phase does not rotate by one rotation over a range from a low frequency region to a high frequency region. Where the characteristics are viewed from another phase, the low frequency characteristic which becomes the center of noise reduction is influenced much by the digital filter section 122, but in the middle and high frequency regions within which the phase rotation is likely to increase by delay of the ADC/DAC section, the characteristic of the analog path which indicates a quick response is used effectively.

Also in the case of FIG. 22B, similarly as in the case of FIG. 20B, if the phase margin for prevention of loop oscillation is 30 degrees (the effective range of the phase is from −150 degrees to 150 degrees) as seen from the graph on the middle stage and the axis of ordinate of the gain is regarded as a relative value, then the characteristic (β characteristic) of the FB filter circuit can be actually shifted on the graph shown on the lowermost stage of FIG. 20B until a horizontal broken line indicated by a thick line comes to new 0 dB.

[Particular Example 3 of the FB Filter Circuit of the Hybrid Feedback Type]

While, in the particular examples 1 and 2 described above, a digital filter section is represented by an IIR filter in order to simplify the description, the digital filter section is not limited to this. For example, an FIR (Finite Impulse Response) filter itself or a composite filter formed from both of IIR and FIR filters connected in parallel or in series may be used. In this instance, also in design of the FIR filter, in order to avoid unnecessary phase rotation as far as possible, it is preferable to design an appropriate gain and then establish a minimum phase transition type. By using a minimum phase transition type FIR filter in this manner, such phase rotation as described above can be avoided and the delay is reduced, and reduction of noise can be achieved with a higher degree of accuracy.

Figure 23:
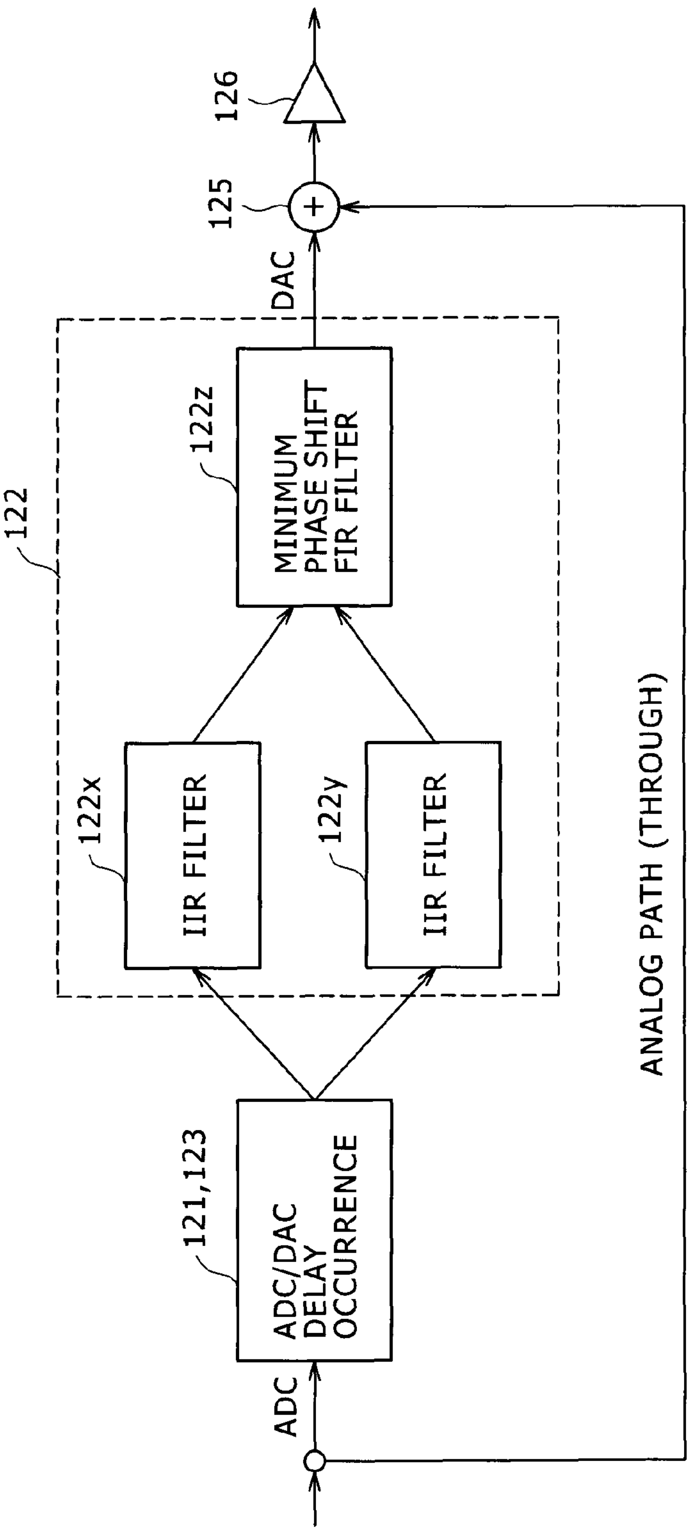
FIG. 23 is a block diagram showing an FB filter circuit having a digital filter section of a composite filter configuration.

FIG. 23 shows an FB filter circuit 12E having a digital filter section 122 of a configuration of a composite filter. Referring to FIG. 23, the FB filter circuit 12E includes a digital filter section 122 wherein an IIR filter 122*x* and another IIR filter 122*y* are provided in parallel and a minimum phase shift type FIR filter 122*z* is provided at a stage following the IIR filters 122*x* and 122*y*. An FB filter circuit having the digital filter section 122 wherein a composite filter is formed using an IIR filter and an FIR filter is formed in this manner.

Further, while, in the FB filter circuits of the particular examples described hereinabove, the comparatively high sampling frequency of 96 kHz is used in order to achieve high noise reduction effects (effective frequency band and effective gain), the sampling frequency is not limited to this. Depending upon the target effect amounts, even if the sampling frequency is lowered, similar noise reduction effects can be anticipated if a noise canceling system of the feedback type which includes an FB filter circuit which includes a digital path and an analog path provided in parallel, that is, a noise canceling system of the hybrid feedback type, is used.

[Applications to a Noise Canceling System]

Now, applications of a noise canceling system which uses an FB filter circuit of the hybrid feedback type according to the present invention are described.

[Application 1 to a Noise Canceling System]

In the noise canceling systems of the feedback type shown in FIGS. 1, 14 and 15, the analog input sound S such as reproduced music, telephone conversation voice, collected sound or the like from the outside which is an object of hearing is added in the form of an analog signal after analog equalization is performed therefor. However, if also the analog input sound S is AD (Analog/Digital) converted and digitally filtered (equalized), then finer sound quality can be implemented with a higher degree of accuracy.

Figure 24:
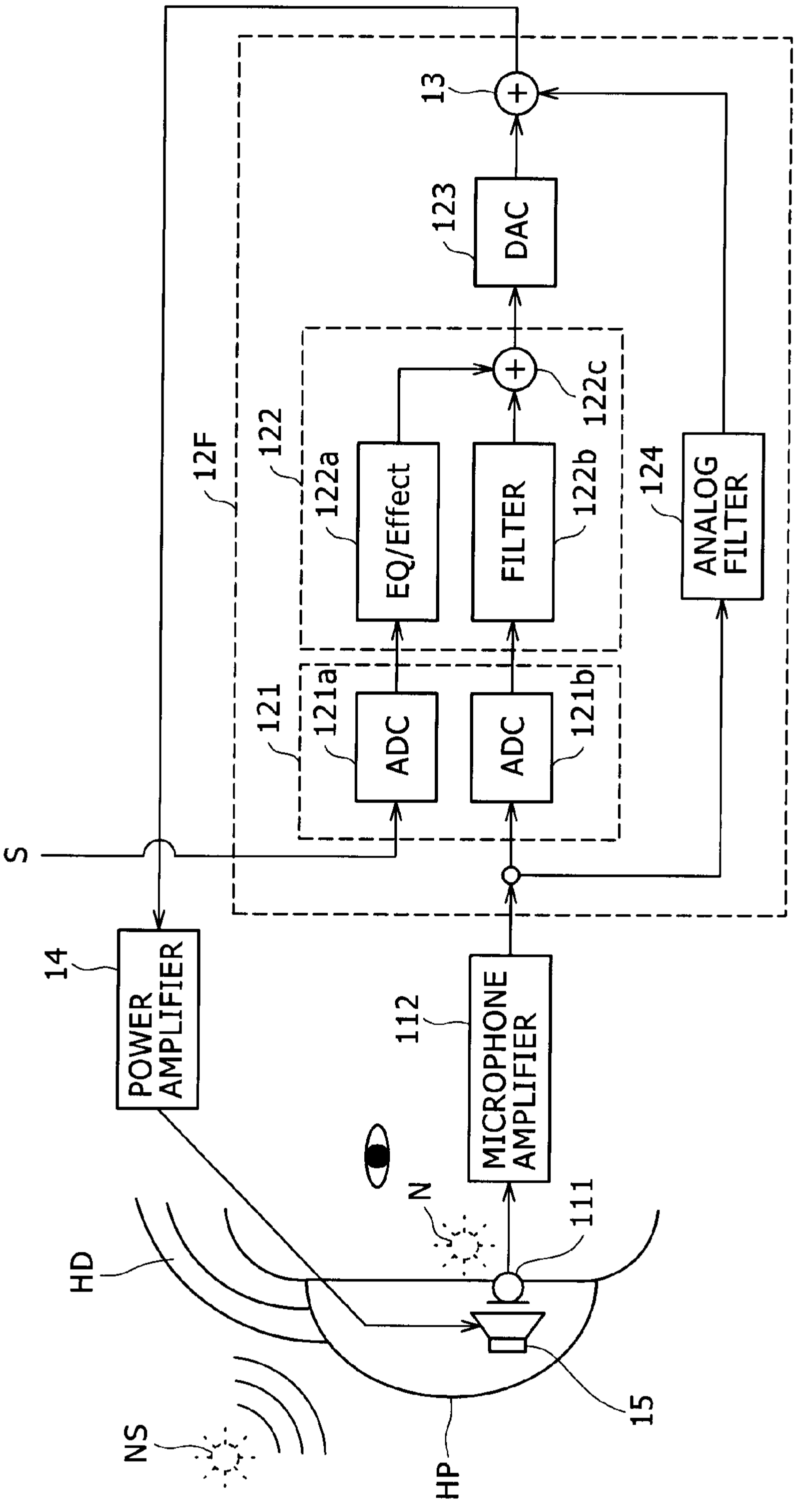
FIG. 24 is a schematic block diagram showing a noise canceling system wherein analog input sound is AD converted so that digital filtering can be performed.

FIG. 24 shows a noise canceling system which is configured so as to AD convert and equalize the analog input sound S. Referring to FIG. 24, a driver 15 formed from a drive circuit 151 and a speaker 152 is provided in the inside of a headphone housing HP of a headphone to be attached the head of the user, that is, to the user head HD. Further, a microphone 111 is provided in the proximity of the position of one of the ears of the user, that is, a cancel point CP, in the inside of the headphone housing HP.

A sound signal collected by and converted into an electric signal by the microphone 111, that is, a noise signal, is amplified by a microphone amplifier 112 and then supplied to an FB filter circuit 12F of the hybrid feedback type which has an analog path. Then, the noise signal is processed by the FB filter circuit 12F to form a noise reduction signal, which is supplied to the driver 15 through a power amplifier 14 so that sound is emitted from the driver 15 thereby to reduce the noise signal.

As seen from FIG. 24, the FB filter circuit 12F is of the hybrid feedback type wherein a digital section formed from an ADC 121, a digital filter section 122 and a DAC 123 and an analog path having an analog filter 124 are provided in parallel to each other. The noise reduction signal converted into an analog signal by the DAC 123 of the digital section and an analog signal from the analog path are synthesized by a synthesis section 13. It is to be noted that an FB filter circuit of the hybrid feedback type is hereinafter referred to as hybrid FB filter circuit.

In the hybrid FB filter circuit 12F of the noise canceling system shown in FIG. 24, the ADC 121 includes an ADC 121*a* for converting the analog input sound S into a digital signal and another ADC 121*b* for converting a collected sound signal from the microphone amplifier 112 into a digital signal.

The DSP/CPU 122 implements an equalizer/effect section 122*a* for the input sound S, a filter section 122*b* for producing a noise reduction signal, and a synthesis section 122*c* for synthesizing output signals from the equalizer/effect section 122*a* and the filter section 122*b*. It is to be noted, in FIG. 24, the equalizer/effect section 122*a* is described as EQ/Effect.

In this manner, since the hybrid FB filter circuit 12F shown in FIG. 24 has one ADC 121*a* separately from the loop for noise reduction, the digital filter section 122 can perform equalization and so forth for the input sound S and can synthesize or mix the input sound S with the noise reduction signal from the loop for noise reduction and supply a resulting signal to the DAC 123.

Since the noise canceling system shown in FIG. 24 is configured in such a manner as described above, also the analog input sound S is AD (Analog/Digital) converted and digitally filtered (equalized and so forth) so that finer sound quality adjustment can be implemented with a higher degree of accuracy and also reduction of noise can be achieved effectively.

Figure 25:
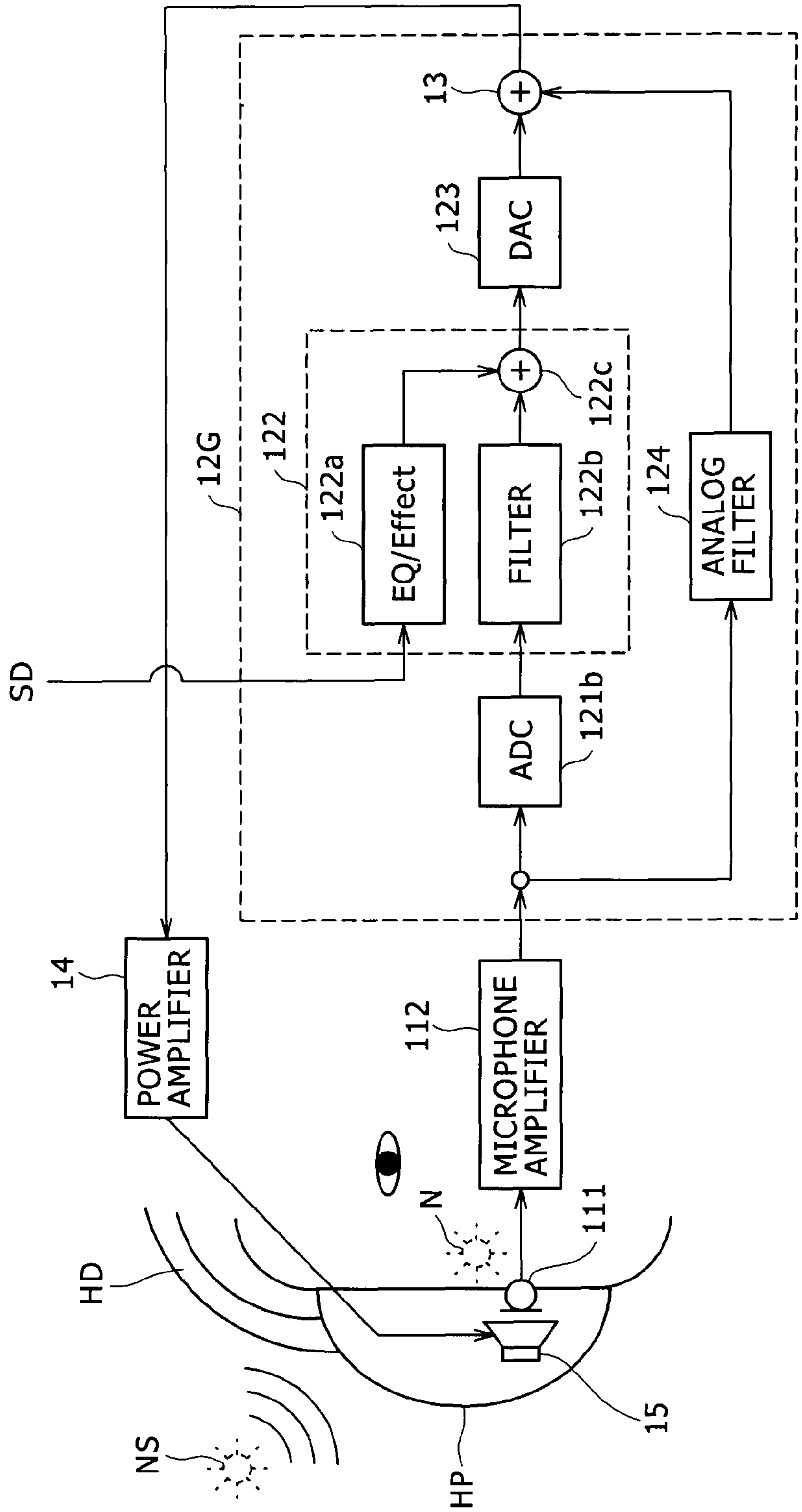
FIG. 25 is a block diagram showing a noise canceling system of the feedback type configured so as to accept digital input sound.

FIG. 25 shows a noise canceling system of the feedback type which is configured so as to accept digital input sound SD. While the noise canceling system shown in FIG. 24 includes the ADC 121*a* in order to accept an input of the input sound S, the input sound S may possibly be inputted after it is digitized by some means.

In this instance, the noise canceling system of the feedback type is configured such that, as shown in FIG. 25, the digital input sound SD is supplied directly to a digital filter section 122 which implements the function of the equalizer/effect section 122*a* which processes the digital input sound SD from the outside.

In particular, the FB filter circuit 12G of the noise canceling system of the feedback type shown in FIG. 25 includes an ADC 121*b*, a digital filter section 122 including an equalizer/effect section 122*a* and a filter section 122*b*, a DAC 123, an analog filter 124 and a synthesis section 13. Accordingly, the FB filter circuit 12G shown in FIG. 25 is configured similarly to the noise canceling system shown in FIG. 24 except that it does not include the ADC 121*a* for the input sound S.

Where the noise canceling system of the feedback type is configured so as to accept supply of the digital input sound SD as seen in FIG. 25, it can appropriately process also the digital input sound SD supplied in a digital form and can effectively implement also reduction of noise.

[Application 2 to a Noise Canceling System]

Figure 26:
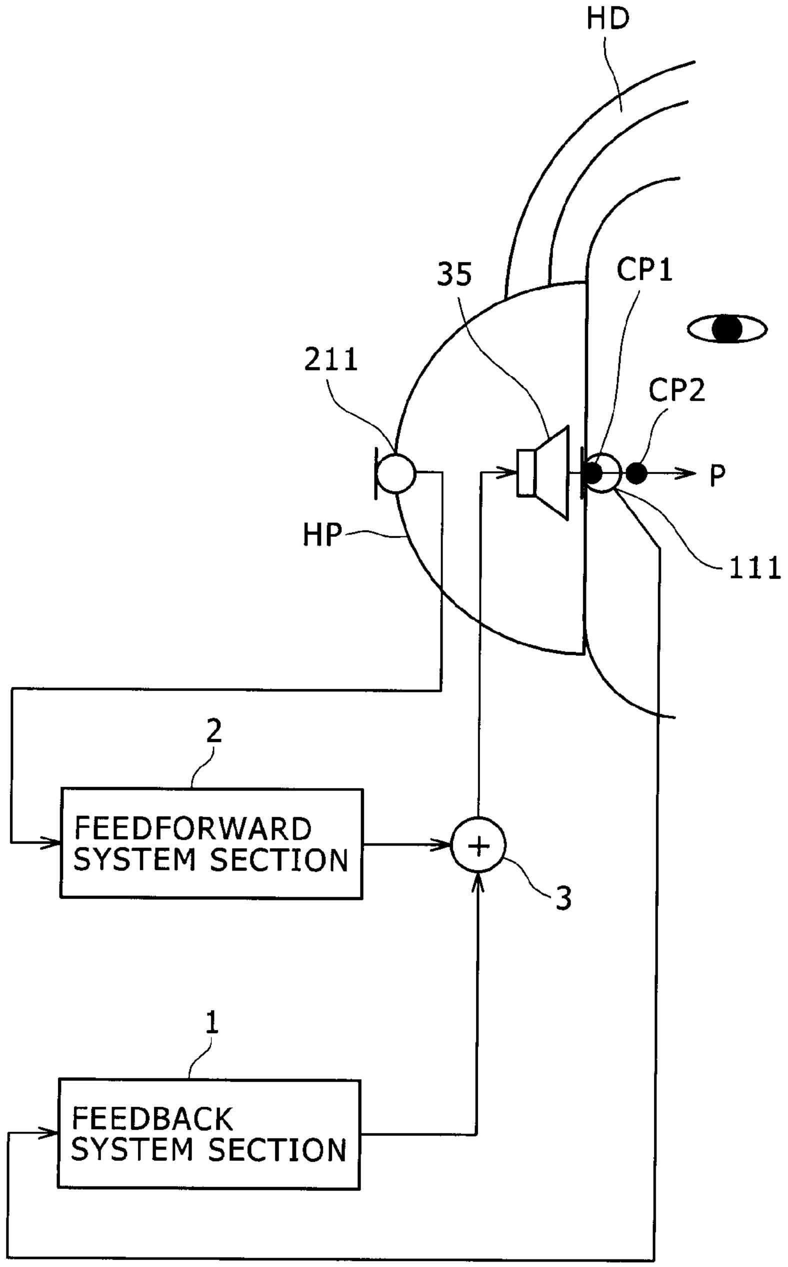
FIG. 26 is a schematic block diagram showing a noise canceling system which includes a combination of a system section of the feedback type and a system section of the feedforward type.

As another application of the present invention, also it is a possible idea to modify the basic configuration of the noise canceling system by which a noise reduction effect is obtained such that it uses a combination of both of the feedback system and the feedforward system. FIG. 26 shows a noise canceling system which includes both of the feedback system and the feedforward system.

Referring to FIG. 26, the noise canceling system shown includes a feedback system section 1 which is a noise canceling system section of the feedback type and a feedforward system section 2 which is a noise canceling system section of the feedforward type.

A sound signal, that is, a noise signal, collected by a microphone 111 provided in the inside of a headphone housing HP which is attached to the user head HD is supplied to the feedback system section 1. The feedback system section 1 produces a noise reduction signal by means of an FB filter section not shown, and the produced noise reduction signal is supplied to a synthesis section 3.

Meanwhile, another sound signal, that is, another noise signal, collected by another microphone 211 provided outside the headphone housing HP which is attached to the user head HD is supplied to the feedforward system section 2. The feedforward system section 2 produces a noise reduction signal by means of an FF filter section, and the produced noise reduction signal is supplied to the synthesis section 3.

The synthesis section 3 synthesizes the noise reduction signal from the feedback system section 1 and the noise reduction signal from the feedforward system section 2 and supplies a resulting noise reduction signal to a driver 35 which includes a drive circuit 351 and a speaker 352 (FIG. 27) so that the driver 35 emits sound in accordance with the noise reduction signal thereby to acoustically reduce the noise which may arrive at the ear of the user.

Since, different from the feedback system, the feedforward system does not basically refer to the sound pressure at a control point and includes a single representative filter fixed upon designing, some noise component may remain, at a cancel point CP2, by more than an amount estimated upon designing also within a reproduction object frequency band depending upon the position of the noise source or the difference in ear characteristic of an individual person. However, where the feedback system wherein the control point of a cancel point CP1 is referred to is used together, also the noise component which may remain after noise reduction by the feedforward system can be canceled. Consequently, increase of the noise reduction effect can be anticipated.

Figure 27:
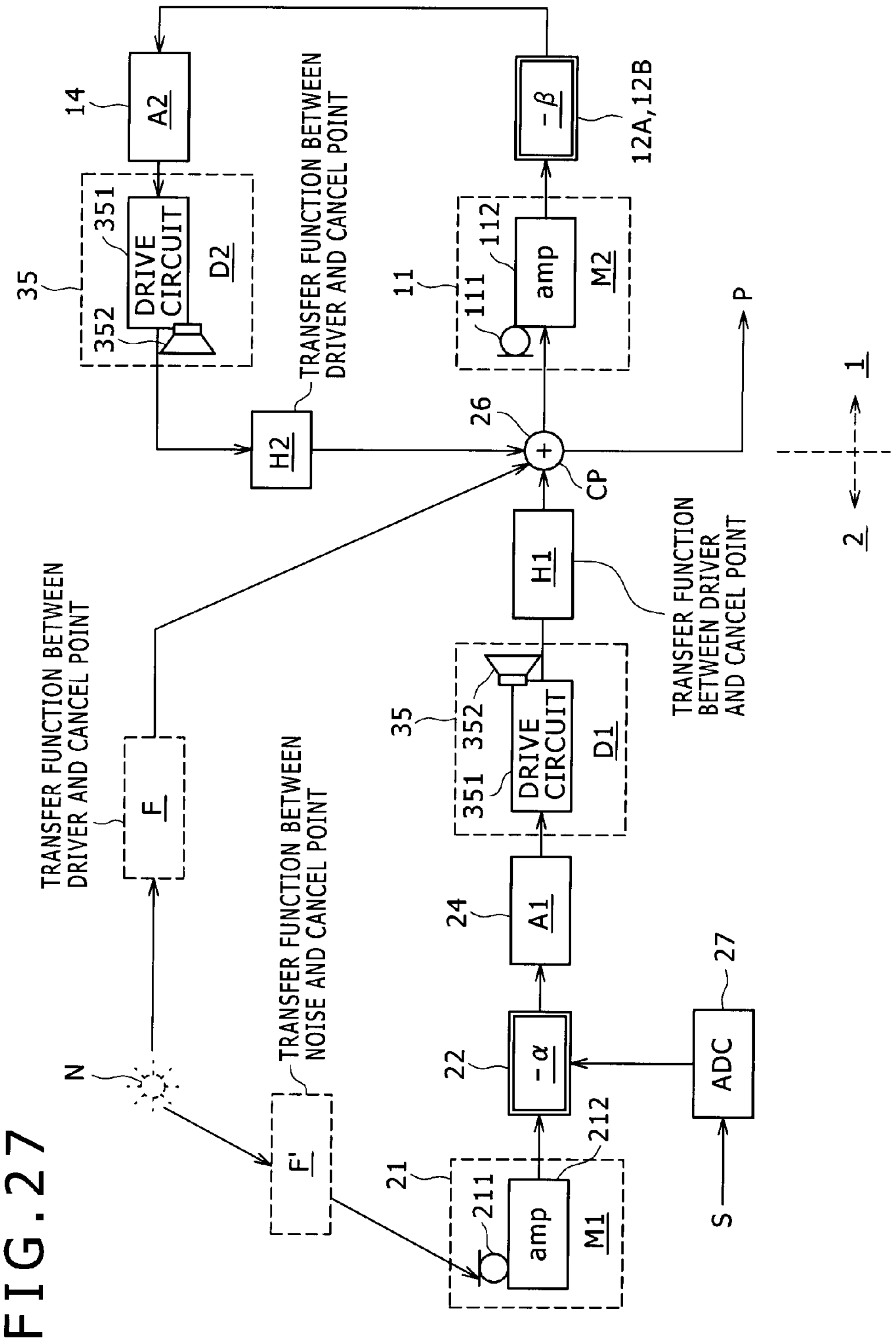
FIG. 27 is a block diagram showing an example of a detailed configuration of the noise canceling system shown in FIG. 26.

FIG. 27 more particularly shows the example of the configuration of the noise canceling system which includes the feedback system section 1 and the feedforward system section 2 shown in FIG. 26.

Referring to FIG. 27, a microphone and microphone amplification section 11, FB filter circuits 12A and 12B, a power amplifier 14 and a driver 35 shown at a right portion of FIG. 27 cooperatively form the feedback system section 1. Meanwhile, a microphone and microphone amplification section 21, an FF filter circuit 22, a power amplifier 24 and a driver 35 shown at a left portion of FIG. 27 cooperatively form the feedforward system section 2.

It is to be noted that, in FIG. 27, in order to clearly indicate the configuration of the feedback system section 1 and the configuration of the feedforward system section 2 distinctly from each other, the driver 35 is shown in both of the feedback system section 1 and the feedforward system section 2. However, as seen in FIG. 26, the driver 35 is used commonly by the feedback system section 1 and the feedforward system section 2.

As described hereinabove with reference to FIG. 26, actually an output of the power amplifier 14 of the feedback system section 1 and an output of the power amplifier 24 of the feedforward system section 2 are synthesized by the synthesis section 3 at a stage preceding to the driver 35, and then a result of the synthesis is supplied to the driver 35. Further, as described hereinabove with reference to FIG. 26, noise which cannot be reduced sufficiently by the function of the feedforward system section 2 can be further reduced by the function of the feedback system section 1.

The most significant point is that, as the configuration of the FB filter circuit shown as the FB filter circuits 12A, 12B, etc. in FIG. 27 uses the hybrid FB filter circuit according to the present invention which has the configuration shown in FIGS. 11, 13A and 13B, more particularly in any of FIGS. 17, 21 and 23, merits achieved by digitalized formation of the FB filter circuit in the feedback system section 1 can be enjoyed and a higher noise reduction effect can be obtained over a wider frequency band.

Further, if the noise canceling system described hereinabove with reference to FIGS. 26 and 27 is viewed from another approach, then the following can be considered. In particular, in the feedforward system, the coefficient for cancellation is basically determined in advance, and the noise reduction amount cannot be increased in accordance with an individual difference in characteristic. In other words, the gain of the cancel signal, that is, the noise reduction signal, is set to a rather lower level.

Therefore, in the noise canceling system described hereinabove with reference to FIGS. 26 and 27, the noise canceling system of the feedback type is used to further increase noise attenuation. In other words, the noise canceling system described hereinabove with reference to FIGS. 26 and 27 achieves an enhanced noise reduction effect by using the feedback system and the feedforward system complementarily.

Figure 28:
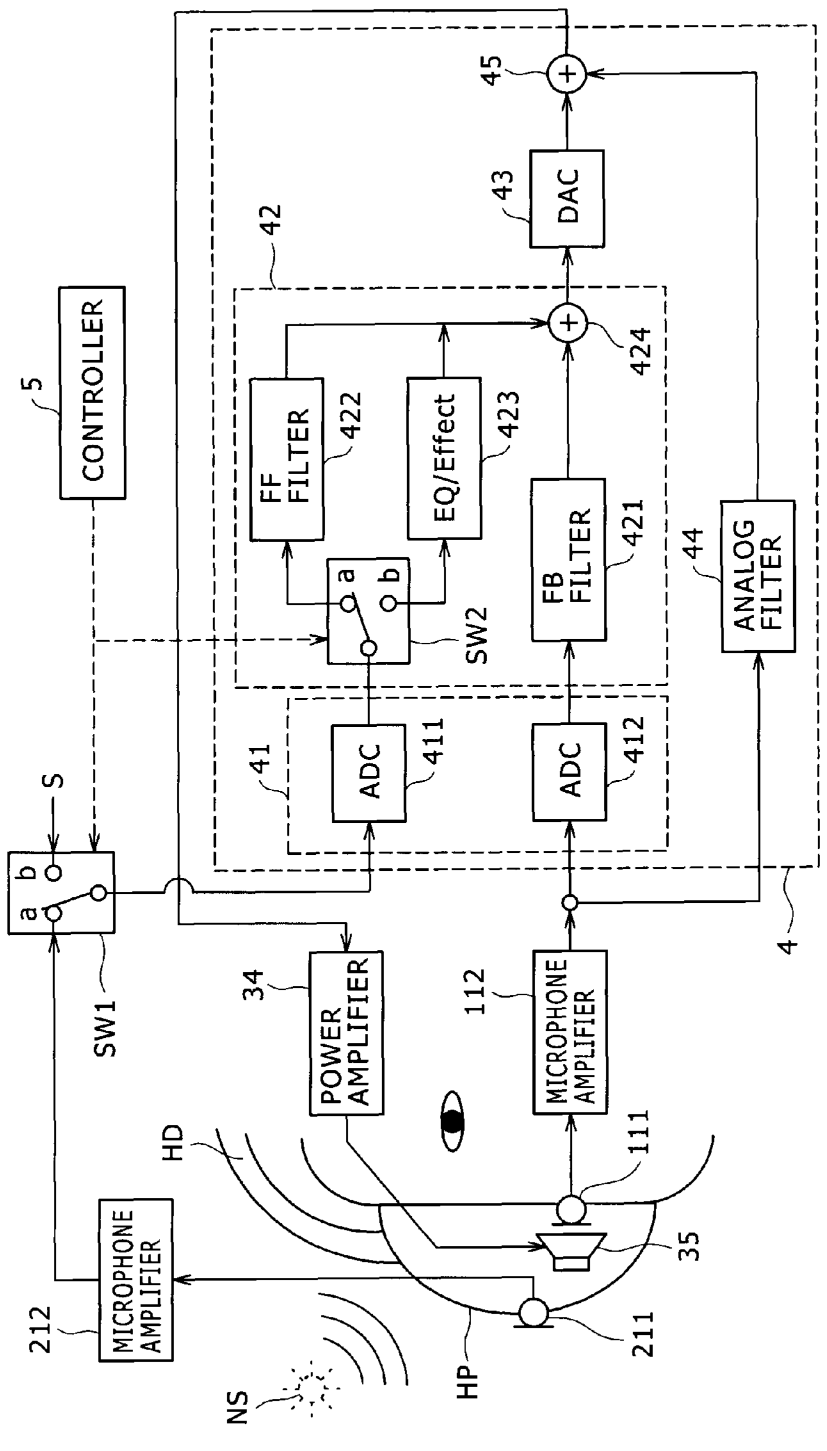
FIG. 28 is a schematic block diagram showing a hybrid FB filter circuit according to the present invention which is applied to a system wherein a feedback system and a feedforward system are used complementarily.

[Application 3 to a Noise Canceling System]

Where a system which uses the feedback system and the feedforward system complementarily is incorporated, it may be configured as a noise canceling system of the configuration shown in FIG. 28 which additionally includes an external inputting section. FIG. 28 shows a system which uses the feedback system and the feedforward system complementarily and to which the hybrid FB filter circuit according to the present invention is applied.

Referring to FIG. 28, a microphone 111 for the feedback system is provided inside a headphone housing HP to be attached to the user head HD, and a microphone 211 for the feedforward system is provided outside the headphone housing HP. A microphone amplifier 112 is provided at a stage following the microphone 111 for the feedback system while a microphone amplifier 212 and a switch circuit SW10 are provided at a stage following the microphone 211 for the feedforward system.

A noise canceling filter circuit 4 is provided at a stage following the microphone amplifier 112 and the switch circuit SW1, and a power amplifier 34 and a driver 35 are provided at a stage following the noise canceling filter circuit 4. The driver 35 includes a drive circuit 351 and a speaker 352.

It is to be noted that the switch circuit SW1 provided at the following stage of the microphone amplifier 212 for the feedforward system has an input terminal a to which a sound signal, that is, a noise signal, is supplied from the microphone amplifier 212 as seen in FIG. 28. The switch circuit SW1 further has another input terminal b to which input sound S in the form of an analog signal is supplied. The switch circuit SW1 thus switches in order to selectively output one of the signals inputted to the input terminals a and b thereof.

Further, although a more detailed description is hereinafter given, the switch circuit SW1 is switched in an interlocking relationship with another switch circuit SW2 provided in the noise canceling filter circuit 4. Then, a controller 5 performs switching control of the switch circuit SW1 and the switch circuit SW2 in response to an operation input from the user accepted through an operation section not shown. Further, the controller 5 not only performs the switching control of the switches SW1 and SW2 but also controls the components of a digital filter section 42 so that an object process can be performed.

Further, the noise canceling filter circuit 4 includes an ADC 41, a digital filter section 42, a DAC 43 and an analog filter 44. The ADC 41 includes an ADC 411 for converting a noise signal from the microphone amplifier 212 or input sound S which are analog signals from the switch circuit SW1 into a digital signal, and an ADC 412 for converting the noise signal from the microphone amplifier 212 into a digital signal.

The digital filter section 42 includes a filter circuit (hereinafter referred to as FB filter) 421 for feedback control, a switch circuit SW2, a filter circuit (hereinafter referred to as FF filter) 422 for feedforward control, an equalizer/effect section 423 (denoted as EQ/Effect in FIG. 28) and a synthesis section 424.

As described hereinabove, the switch circuits SW1 and SW2 are switched in an interlocking relationship with each other by the controller 5. In particular, when the switch circuit SW1 is changed over to the input terminal a side, also the switch circuit SW2 is changed over to the input terminal a side, but when the switch circuit SW1 is changed over to the input terminal b side, also the switch circuit SW2 is changed over to the input terminal b side.

Accordingly, if the switch circuit SW1 is changed over to the input terminal a side, also the switch circuit SW2 is changed over to the input terminal a side. In this instance, a sound signal, that is, a noise signal, collected by the microphone 211 is amplified by the microphone amplifier 212 and then supplied to the ADC 411 through the switch circuit SW1. Then, the sound signal is converted into a digital signal by the ADC 411 and then supplied to the FF filter 422 through the switch circuit SW2. The FF filter 422 forms a noise reduction signal, that is, a cancel signal, for the feedforward system from the noise signal supplied thereto and supplies the noise reduction signal to the synthesis section 424.

Meanwhile, a sound signal, that is, a noise signal, collected by the microphone 111 is amplified by the microphone amplifier 112 and then supplied to the ADC 412 and the analog filter 44. The ADC 412 converts the sound signal supplied thereto into a digital signal and supplies the digital sound signal to the FB filter 421. The FB filter 421 forms a noise reduction signal, that is, a cancel signal, for the feedforward system from the noise signal supplied thereto and supplies the formed noise reduction signal to the synthesis section 424.

The synthesis section 424 synthesizes the noise reduction signal for the feedforward system from the FF filter 422 and the noise reduction signal for the feedforward system from the FB filter 421 and supplies a resulting signal to the DAC 43. The DAC 43 converts the noise reduction signal supplied thereto into an analog signal and supplies the analog noise reduction signal to the synthesis section 45.

Also an analog signal obtained by an analog filtering process by the analog filter 44 is supplied to a synthesis section 45. The synthesis section 45 thus synthesizes the noise reduction signal from the DAC 43 and the noise reduction signal after analog processing from the analog filter 44 and supplies a resulting signal to the power amplifier 34. The power amplifier 34 amplifiers the noise reduction signal supplied thereto and supplies the amplified noise reduction signal to the driver 35. Consequently, a noise cancel signal is emitted from the driver 35 so that the noise is reduced acoustically.

Where the switch circuits SW1 and SW2 are changed over to the input terminal a side in this manner, the ADC 411, FF filter 422 and DAC 43 cooperatively form an FF filter circuit, and the microphone 211, microphone amplifier 212, switch circuit SW1, ADC 411, switch circuit SW2, FF filter, synthesis section 424, DAC 43, synthesis section 45, power amplifier 34 and driver 35 cooperatively form a noise canceling system of the feedforward type.

Simultaneously, the ADC 412, FB filter 421, DAC 43 and analog filter 44 cooperatively form an FB filter circuit, and the microphone 111, microphone amplifier 112, ADC 412, FB filter 421, synthesis section 424, DAC 43, analog filter 44, synthesis section 45, power amplifier 34 and driver 35 cooperatively form a noise canceling system of the feedback type.

In this manner, where the switch circuits SW1 and SW2 are changed over to the input terminal a side, since the noise canceling system section of the feedforward type functions and also the noise canceling system section of the feedback type having a hybrid FB filter circuit which in turn has a digital path and an analog path functions, noise is suppressed satisfactorily and a no-sound state of a high degree of quality can be formed.

On the other hand, where the switch circuits SW1 and SW2 are changed over to the input terminal b side, the input sound S is supplied to the ADC 411 through the switch circuit SW1. Consequently, the input sound S is converted into a digital signal by the ADC 411 and is then supplied to the equalizer/ effect section 423 through the switch circuit SW2. The input sound S is thus subjected to fine sound quality adjustment with a high degree of accuracy by the equalizer/effect section 423 and is then supplied to the synthesis section 45. The synthesis section 45 synthesizes the input sound S from the equalizer/effect section 423 with the noise reduction signal for the feedback system and outputs a resulting signal.

In this manner, where the switch circuits SW1 and SW2 are changed over to the input terminal b side, a signal formed by synthesis of the input sound S after sound quality adjustment and the noise reduction signal for the feedback system is converted into an analog signal by the DAC 43. Further, the analog signal from the DAC 43 is synthesized with a noise reduction signal after analog processing from the analog filter 44 by the synthesis section 45. Then, a signal obtained by the synthesis by the synthesis section 45 is supplied through the power amplifier 34 to the driver 35, from which sound is emitted. In this instance, sound according to the input sound whose sound quality is adjusted with a high degree of accuracy is reproduced well while noise is reduced using the noise canceling system of the feedback type so as to be heard by the user.

Thus, the noise canceling system shown in FIG. 28 can be summarized in the following manner. In particular, the noise canceling system processes three signals including a sound signal (feedback microphone signal) corrected by the microphone 111, another sound signal (feedforward microphone signal) collected by the microphone 211 and an external input signal (input sound S). Therefore, although three ADCs are originally required, in the noise canceling system of the configuration described above with reference to FIG. 28, changeover between the feedforward microphone signal and the input sound S is performed at a stage preceding to the ADCs.

Consequently, if the user wants a quiet environment, then the input sound S is not reproduced while the two different noise reduction mechanisms, that is, the noise canceling system of the feedback type and the noise canceling system of the feedforward type, are operated at the same time. On the other hand, when the user hears external input sound, that is, the input sound S, only the noise canceling system of the feedback type is operated. In this manner, a system can be implemented wherein the noise canceling system or systems to be operated can be changed over.

It is to be noted that, for the simplification of the system shown in FIG. 28, it is possible to form the noise canceling system of the feedforward type in FIG. 28 from analog circuits or set a noise canceling system which performs switching with the input sound S of an external input to the noise canceling system of the feedback type side.

[Variations to the Combination of the Noise Canceling Systems]

Here, variations to noise canceling systems to which the present invention can be applied are summarized. A hybrid filter circuit which includes a digital section and an analog path provided in parallel and synthesizes an output of the digital section and an output of the analog path both as analog signals to produce a noise reduction signal or canceling signal can be applied to (1) an FB filter circuit of a noise canceling system of the feedback type and (2) an FF filter circuit of a noise canceling system of the feedforward type.

In the case of a noise canceling system which includes both of a noise canceling system of the feedback type and a noise canceling system of the feedforward type, if the hybrid filter circuit according to the present invention is used as a filter circuit for one of the noise canceling systems, it is possible to use, as the filter circuit for the other noise canceling system, an existing analog filter or the hybrid filter circuit according to the present invention in which digital and analog filters are provided in parallel.

Further, not only in a noise canceling system of the feedback type which includes a hybrid FB filter circuit as described hereinabove with reference to FIG. 28, but also in a system wherein a noise canceling system of the feedforward type and an input sound reproduction processing section which includes the ADC 411, equalizer/effect section 423 and so forth for processing input sound from the outside can be used switchably, it is possible to use, as the FF filter circuit of the noise canceling system of the feedforward type, an existing analog filter, a digital filter, or the hybrid filter circuit according to the present invention in which digital and analog filters are provided in parallel.

Similarly, not only in a noise canceling system of the feedforward type which includes a hybrid FF filter circuit, but also in a system wherein a noise canceling system of the feedback type and an input sound reproduction processing section which includes an ADC, an equalizer/effect section and so forth for processing input sound from the outside can be used switchably, it is possible to use, as the FB filter circuit of the noise canceling system of the feedback type, an existing analog filter, a digital filter, or the hybrid filter circuit according to the present invention in which digital and analog filters are provided in parallel.

Further, also where the hybrid filter circuit according to the present invention is applied to an FB filter circuit and also where it is applied to an FF filter circuit, it may have various configurations as described hereinabove in connection with the FB filter circuits 12A to 12G. In a word, it is necessary for a filter circuit to have a hybrid configuration wherein a digital section and an analog path are connected in parallel and an output of the digital section and an output of the analog path are synthesized as analog signals to produce a noise reduction signal or canceling signal.

[Summary]

From the foregoing, a noise canceling system of the feedback type which includes a microphone mechanism inside a headphone for reducing noise in the headphone is implemented by configuring the noise canceling system of the feedback type such that an FB filter circuit (feedback filter) which keeps stabilization of the system and determines a noise attenuation amount is formed from a parallel connection of a digital section including an ADC, a DSP/CPU section and a DAC and an analog path having an analog filter or an analog path (analog through-pass) of a through-characteristic principally in order to suppress phase rotation and outputs of the digital section and the analog path are added in an analog mode.

In this instance, the analog filter of the analog path connected in parallel to the digital section may be of a simple configuration such as that of a first-order LPF or HPF or may be of the type which does not have a frequency characteristic and can produce a signal which can be directly added in an analog mode to an output result from the digital section.

Also it is possible to use an FIR of the minimum phase shift type as some or all of filters in the digital section connected in parallel to the analog path.

Also it is possible to form a no-sound state of a high degree of quality by configuring a noise canceling system of the twin type in which a noise canceling system of the feedback type including an FB filter circuit in which the digital section and the analog path described above are connected in parallel and an analog or digital noise canceling system of the feedforward type which uses a microphone provided outside a headphone housing or such analog and digital noise canceling systems of the feedforward type connected in parallel are used simultaneously.

Also it is possible to configure a system having a control section which has a mode wherein a noise reduction system wherein outputs of both of a microphone inside the headphone housing and the microphone outside the headphone housing are inputted to an ADC such that they are digitally processed later is configured and another mode wherein one of the microphone signals from the microphones inside and outside the headphone housing is switched to an external signal (music signal, telephone conversation signal or the like) to connect the signals to the same ADC and an instruction is issued to the DSP/CPU to change the applicable program from the noise reduction program to an equalizer program.

[Others]

While the present invention is described above in connection with processing of a headphone for the simplified description, it is not necessary for all components to be incorporated in the headphone body, but the present invention can be applied also where, for example, the processing mechanism is divisionally provided in a box outside the headphone body or the headphone body is combined with a different apparatus. The different apparatus here may be various types of hardware which can reproduce a sound or music signal such as, for example, a portable audio player, a telephone apparatus and a network sound communication apparatus.

Naturally, also it is possible to apply the present invention to a noise canceling system of a headset which is used to work at a place which is very noisy such as a factory or an airport for reducing the noise. Furthermore, where the present invention is applied to a portable telephone set, telephone conversation by clear sound can be anticipated also in a noisy environment. Where the present invention is applied to a portable audio player, clear music or the like can be enjoyed also in a noisy environment.

Further, in the embodiment described hereinabove, an FB filter circuit of a noise canceling system of the feedback type is configured as a hybrid noise canceling system wherein a digital section and an analog path are connected in parallel. However, it is possible to form not only an FB filter circuit but also an FF filter of a noise canceling system of the feedforward type as a hybrid nose canceling system wherein a digital section and an analog path are connected in parallel.

While a preferred embodiment of the present invention has been described using specific terms, such description is for illustrative purpose only, and it is to be understood that changes and variations may be made without departing from the spirit or scope of the following claims.

What is claimed is:

1. A filter circuit for producing a noise reduction signal for reducing a noise signal collected by a microphone, comprising:
- a digital section including
  - an analog/digital conversion section configured to convert the noise signal into a digital noise signal,
  - a digital filter section including in parallel a low pass filter and mid presence filter to each process the digital noise signal to produce digital noise reduction signals based on the digital noise signal, and
  - a digital/analog conversion section configured to convert the digital noise reduction signals into analog noise reduction signals;
- an analog path connected in parallel to said digital section and configured to output, as an unfiltered analog signal, the noise signal; and
- a synthesis section configured to synthesize the analog noise reduction signals out putted from said digital/analog conversion section of said digital section and the unfiltered analog signal outputted from said analog path to produce the noise reduction signal to reduce noise.

2. The filter circuit according to claim 1, wherein said digital filter section of said digital section includes a minimum phase shift type finite impulse response filter.

3. The filter circuit according to claim 1, wherein said digital section and said analog path receive the noise signal through the microphone which is provided inside a headphone housing, the noise signal being used in a noise canceling system of a feedback type.

4. The filter circuit according to claim 1, wherein said digital sect ion and said analog path receive the noise signal through the microphone which is provided outside a headphone housing, the noise signal being used in a noise canceling system of the feedforward type.

5. The filter circuit according to claim 1, wherein the digital filter section further includes a second mid presence filter to receive and process the digital noise reduction signals.

6. The filter circuit according to claim 5, wherein the digital filter section further includes a third mid presence filter to receive and process the digital noise reduction signals output from the second mid presence filter.

7. A noise reduction signal production method used in a noise canceling system for producing a noise reduction signal to reduce noise in response to receiving a noise signal through a microphone, comprising:
- converting, at an analog/digital conversion section of a digital section, the noise signal into a digital noise signal;
- producing, via a digital filter section of the digital section including in parallel a low pass filter and mid presence filter to each process the digital noise signal, digital noise reduction signals based on the digital noise signal; and
- converting, at a digital/analog conversion section of the digital section, the digital noise reduction signals into analog noise reduction signals;
- outputting, as an unfiltered analog signal and via an analog path connected in parallel to the digital section, the noise signal; and
- synthesizing, at a synthesis section, the analog noise reduction signals and the unfiltered analog signal to produce the noise reduction signal to reduce noise.

8. The noise reduction signal production method according to claim 7, wherein the noise reduction signal formed by the digital filter section is formed via a minimum phase shift type finite impulse response filter.

9. The noise reduction signal production method according to claim 7, wherein
- the noise reduction signal production method is used in a noise canceling system of the feedback type, and
- the noise signal is collected through the microphone which is provided inside a headphone housing.

10. The noise reduction signal production method according to claim 7, wherein the noise reduction signal production method is used in a noise canceling system of the feedforward type, and
- the noise signal is collected through the microphone which is provided outside a headphone housing.

11. A noise canceling system of the feedback type, comprising:
- a microphone configured to collect a noise signal leaking into the inside of a housing and configured to attach to an ear portion of a user;

a filter circuit configured to form a noise reduction signal to reduce noise from the noise signal collected by said microphone;

an amplification section configured to amplify the noise reduction signal formed by said filter circuit; and a driver configured to emit sound into the housing based on the noise reduction signal from said amplification section;

said filter circuit including a digital section that includes an analog/digital conversion section configured to receive the noise signal and convert the noise signal into a digital noise signal, a digital filter section including in parallel a low pass filter and mid presence filter configured to receive the digital noise signal from said analog/digital conversion section and to each process the digital noise signal to produce noise reduction signals from the digital noise signal, and a digital/analog conversion section configured to receive the digital noise reduction signals from said digital filter section and convert the digital noise reduction signals into analog noise reduction signals, said filter circuit further including an analog path connected in parallel to said digital section and configured to output, as an unfiltered analog signal, the noise signal collected by said microphone, and a synthesis section configured to synthesize the noise reduction signals outputted from said digital/analog conversion section of said digital section and the unfiltered analog signal outputted from said analog path to produce the noise reduction signal to reduce noise.

12. The noise canceling system according to claim 11, further comprising:

a sound quality adjustment section configured to receive a sound signal of an object of reproduction and to perform sound quality adjustment based on the sound signal;

a reproduction sound amplification section configured to receive the sound signal having the adjusted sound quality from said sound quality adjustment section and amplify the received sound signal; and a reproduction driver configured to receive the sound signal amplified by said reproduction sound amplification section and emit sound into the inside of said housing in response to receiving the sound signal.

13. The noise canceling system according to claim 11, further comprising:

a noise canceling system section of the feedforward type having:

a second microphone provided outside the housing to collect a second noise signal from a noise source and configured to attach to an ear portion of a user;

a second filter circuit configured to form a second noise reduction signal for reducing noise from the second noise signal collected by said second microphone;

a second amplification section configured to amplify the second noise reduction signal formed by said second filter circuit; and a second driver configured to emit sound into the housing based on the second noise reduction signal from said second amplification section.

14. The noise canceling system according to claim 13, further comprising:

an input sound reproduction processing section including a sound quality adjustment section configured to receive a sound signal of an object of reproduction and to perform sound quality adjustment based on the sound signal, a reproduction sound amplification section configured to receive the sound signal having the adjusted sound quality from said sound quality adjustment section and amplify the received sound signal; and a reproduction driver configured to receive the sound signal amplified by said reproduction sound amplification section and emit sound into the inside of said housing in response to receiving the sound signal; and a changeover section configured to selectively render said noise canceling system section of the feedforward type and said input sound reproduction processing section operative.

15. The noise canceling system according to claim 13, wherein said second filter circuit has a configuration of an analog filter or a digital filter which includes a second analog/digital conversion section configured to receive the second noise signal collected by said second microphone, a second digital filter section configured to receive supply of the digital noise signal from said second analog/digital conversion section to form a noise reduction signal and a second digital/analog conversion section configured to receive supply of the noise reduction signal from said second digital filter section and convert the noise reduction signal into an analog signal, or a configuration which includes a second analog path connected in parallel to the configuration of the digital filter and configured to output the noise signal collected by said second microphone as it is or after processed by an analog filter and synthesizes an output of said digital filter and an output of said analog path.

16. The noise canceling system according to claim 11, wherein said digital filter section of said digital section includes a minimum phase shift type finite impulse response filter.

17. A noise canceling system of the feedforward type, comprising:

a microphone disposed outside a housing to collect a noise signal from a noise source and configured to attach to an ear portion of a user;

a filter circuit configured to form a noise reduction signal to reduce noise from the noise signal collected by said microphone;

an amplification section configured to amplify the noise reduction signal formed by said filter circuit; and a driver configured to emit sound into the housing based on the noise reduction signal from said amplification section;

said filter circuit including a digital section which includes an analog/digital conversion section configured to receive the noise signal collected by said microphone and convert the noise signal into a digital noise signal, a digital filter section including in parallel a low pass filter and mid presence filter configured to receive the digital noise signal from said analog/digital conversion section and to each process the digital noise signal to produce noise reduction signals from the digital noise signal, and a digital/analog conversion section configured to receive the noise reduction signals from said digital filter section and convert the noise reduction signals into analog noise reduction signals, said filter circuit further including an analog path connected in parallel to said digital section and configured to output, as an unfiltered analog signal, the noise signal collected by said microphone, and a synthesis section configured to synthesize the analog noise reduction signals outputted from said digital/analog conversion section of said digital section and the unfiltered analog signal outputted from said analog path to produce the noise reduction signal to reduce noise.

18. The noise canceling system according to claim 17, further comprising:

a noise canceling system of the feedback type including a second microphone provided inside the housing to collect a second noise signal leaking into said housing and configured to attach to an ear portion of a user;

a second filter circuit configured to form a second noise reduction signal for reducing noise from the second noise signal collected by said second microphone;

a second amplification section configured to amplify the second noise reduction signal formed by said second filter circuit; and a second driver configured to emit sound into the housing based on the second noise reduction signal from said second amplification section.

19. The noise canceling system according to claim 18, further comprising:

an input sound reproduction processing section including a sound quality adjustment section configured to receive a sound signal of an object of reproduction and perform sound quality adjustment based on the sound signal, a reproduction sound amplification section configured to receive the sound signal having the adjusted sound quality from said sound quality adjustment section and amplify the received sound signal, and a reproduction driver configured to receive the sound signal amplified by said reproduction sound amplification section and emit sound into the inside of said housing in response to receiving the sound signal; and a changeover section configured to selectively render said noise canceling system section of the feedback type and said input sound reproduction processing section operative.

20. The noise canceling system according to claim 18, wherein said second filter circuit has a configuration of an analog filter or a digital filter which includes a second analog/digital conversion section configured to receive supply of the second noise signal collected by said second microphone, a second digital filter section configured to receive supply of the digital noise signal from said second analog/digital conversion section to form a noise reduction signal and a second digital/analog conversion section configured to receive supply of the noise reduction signal from said second digital filter section and convert the noise reduction signal into an analog signal, or a configuration which includes a second analog path connected in parallel to the configuration of the digital filter and configured to output the noise signal collected by said second microphone as it is or after processed by an analog filter and synthesizes an output of said digital filter and an output of said analog path.

21. The noise canceling system according to claim 17, further comprising:

a sound quality adjustment section configured to receive a sound signal of an object of reproduction and perform sound quality adjustment based on the sound signal;

a reproduction sound amplification section configured to receive the sound signal having the adjusted sound quality from said sound quality adjustment section and amplify the received sound signal; and a reproduction driver configured to receive the sound signal amplified by said reproduction sound amplification section and emit sound into the inside of said housing in response to receiving the sound signal.

22. The noise canceling system according to claim 17, wherein said digital filter section of said digital section includes a minimum phase shift type finite impulse response filter.

* * * * *